US012751754B2

(12) United States Patent
Schmitt et al.

(10) Patent No.: US 12,751,754 B2
(45) Date of Patent: Oct. 6, 2026

(54) CONTROLLING IMPACT DIRECTION OF SURGICAL IMPACTING TOOLS

(71) Applicant: DePuy Synthes Products, Inc., Raynham, MA (US)

(72) Inventors: Eric Schmitt, Palm Beach Gardens, FL (US); Matthew S. Wallace, Wellington, FL (US); Patrick J. Cannon, Warsaw, IN (US); Jon M. Edwards, Stuart, FL (US); Amisiddhi Vilas Bhosale, Wood-Ridge, NJ (US); Thomas Philipson, Palm City, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 599 days.

(21) Appl. No.: 18/168,801

(22) Filed: Feb. 14, 2023

(65) Prior Publication Data

US 2024/0268817 A1 Aug. 15, 2024

(51) Int. Cl.

| | |
|---|---|
| ***A61B 17/92*** | (2006.01) |
| *A61B 17/00* | (2006.01) |
| *A61B 17/16* | (2006.01) |

(52) U.S. Cl.

CPC .... *A61B 17/92* (2013.01); *A61B 2017/00017* (2013.01); *A61B 2017/00367* (2013.01); *A61B 2017/00398* (2013.01); *A61B 17/164* (2013.01); *A61B 17/1659* (2013.01)

(58) Field of Classification Search

CPC ............ A61B 17/1657; A61B 17/1659; A61B 17/1664; A61B 17/1684

See application file for complete search history.

(56) References Cited

U.S. PATENT DOCUMENTS

| | | | | |
|---|---|---|---|---|
| 8,393,409 | B2 | 3/2013 | Pedicini | |
| 8,695,726 | B2 | 4/2014 | Pedicini | |
| 8,894,654 | B2 * | 11/2014 | Anderson | B25B 21/002 173/176 |
| 8,936,105 | B2 | 1/2015 | Pedicini | |
| 9,624,098 | B2 | 4/2017 | Rosenblatt et al. | |
| 10,912,597 | B2 | 2/2021 | Pedicini | |
| 11,013,503 | B2 | 5/2021 | Pedicini | |
| 11,083,512 | B2 | 8/2021 | Pedicini | |
| 11,134,962 | B2 | 10/2021 | Pedicini | |
| 11,426,180 | B2 * | 8/2022 | O'Brien | A61B 17/162 |
| 11,529,180 | B2 * | 12/2022 | Russell | A61B 17/162 |
| 12,279,779 | B2 * | 4/2025 | Gilhooley | B25J 9/1628 |
| 2013/0144296 | A1 | 6/2013 | Yoko et al. | |

(Continued)

OTHER PUBLICATIONS

U.S. Appl. No. 18/435,002, filed Feb. 7, 2024, Eric Schmitt et al.

(Continued)

*Primary Examiner* — Nicholas W Woodall

(74) *Attorney, Agent, or Firm* — Troutman Pepper Locke LLP

(57) ABSTRACT

In general, devices, systems, and methods for controlling impact direction of surgical impacting tools are provided. In an exemplary implementation, a handpiece of a surgical impacting tool includes at least one actuator configured to be actuated by a user to control a direction of impacting. The surgical impacting tool handpiece, such as a handpiece of an orthopedic impactor, is configured to drive impacting of the surgical implement relative to bone.

20 Claims, 14 Drawing Sheets

(56) References Cited

U.S. PATENT DOCUMENTS

| | | | | |
|---|---|---|---|---|
| 2013/0161050 | A1 | 6/2013 | Pedicini | |
| 2015/0351820 | A1* | 12/2015 | Straslicka | A61B 17/1697 606/169 |
| 2017/0360575 | A1 | 12/2017 | Behzadi et al. | |
| 2020/0289134 | A1 | 9/2020 | Laughlin et al. | |
| 2021/0052285 | A1 | 2/2021 | Carusillo | |
| 2022/0008087 | A1 | 1/2022 | Laughlin et al. | |
| 2022/0102995 | A1 | 3/2022 | Fieldbinder et al. | |
| 2022/0226033 | A1* | 7/2022 | Slocum | A61F 2/4603 |
| 2022/0241045 | A1* | 8/2022 | Carusillo | A61B 17/1615 |
| 2022/0361934 | A1 | 11/2022 | Pedicini | |

OTHER PUBLICATIONS

International Search Report and Written Opinion for Intl. Pat. App. No. PCT/IB2024/051322 mailed Apr. 24, 2024. (17 pages).

Medical Enterprises Distribution, Instructions For Use (IFU) ME1000 Adapters, dated Apr. 20, 2017. (60 pages).

U.S. Appl. No. 18/487,326, "Surgical Impacting Tool Couplings" filed Oct. 16, 2023. (63 pages).

* cited by examiner

CONTROLLING IMPACT DIRECTION OF SURGICAL IMPACTING TOOLS

FIELD

The present disclosure generally relates to controlling impact direction of surgical impacting tools.

BACKGROUND

In the field of orthopedics, prosthetic devices, such as artificial joints, are often implanted or seated in a patient's bone cavity. The cavity is typically formed during surgery before a prosthetic device is seated or implanted by, for example, a physician or other medical professional removing and/or compacting existing bone to form the cavity. The prosthetic device, which can also be referred to as a prosthesis, usually includes a stem or other protrusion that is inserted into the cavity.

To create the cavity, a physician or other medical professional may use a broach, chisel, or other surgical implement conforming to the shape of the stem of the prosthetic device. In general, the surgical implement is impelled into the implant area to form the cavity. One technique for impelling the surgical implement includes a physician or other medical professional manually hammering the surgical impacting tool to impel the surgical implement into the implant area. Another technique for creating the prosthetic cavity relies on computer-controlled robotic arms for creating the cavity instead of using manual power provided by a physician or other medical professional. Another technique for creating the prosthetic cavity is to drive the surgical implement pneumatically, e.g., by compressed air. Another technique for creating the prosthetic cavity relies on a linear compressor to compress air on a single stroke basis and then, after a sufficient pressure is created, to release the air through a valve and onto a striker to impel the surgical implement.

An orthopedic impacting tool for orthopedic impacting in hips, knees, shoulders, etc. can hold the surgical implement and drive the impacting of the surgical implement. The impacting tool can be configured for bidirectional impacting in which the surgical implement can be driven in a forward direction, e.g., toward the implant area, or in a reverse direction, e.g., away from the implant area. However, it can be difficult for a physician or other medical professional holding the impacting tool to control whether the surgical implement is driven in the forward direction or the reverse direction.

The impacting tool may be held by a physician or other medical professional at any number of different orientations relative to the implant area so the surgical implement is positioned properly relative to the implant area. The physician or other medical professional having to move the impacting tool relative to the implant area to effect a change in direction of impacting may cause the surgical implement to shake or otherwise move in unintentional direction(s) and thus cause patient harm and/or adversely affect cavity formation, and/or may hinder cavity formation by not allowing the surgical implement to receive and be impelled at full intended force. Additionally, it may be difficult for the physician or other medical professional to move the impacting tool relative to the implant area to change direction of impacting due to the typically heavy weight of impacting tools, especially in instances when the impacting tool is being held at an inverted or other awkward orientation relative to the implant area.

Accordingly, there remains a need for improved surgical impacting tools.

SUMMARY

In general, devices, systems, and methods for controlling impact direction of surgical impacting tools are provided.

In one aspect, a surgical device is provided that in one implementation includes a handpiece configured to be held by a hand and configured to drive impacting of bone. The handpiece includes a first actuator configured to be hand-actuated and thereby cause the impacting to be in a forward direction toward the bone, and a second actuator configured to be hand-actuated and thereby cause the impacting to be in a rearward direction away from the bone. The first and second actuators are configured to be actuated independently of one another.

The surgical device can have any number of variations. For example, the handpiece can include a handle configured to be held by the hand, and the first and second actuators can each be on one of a forward side of the handle and a rearward side of the handle.

For another example, the handpiece can include a third actuator configured to be hand-actuated and thereby cause the impacting to be in a rearward direction away from the bone. Further, the handpiece can include a body and a handle extending from the body, the handle can be configured to be held by the hand, one of the second and third actuators can be on the handle, and the other of the second and third actuators can be on the body.

For yet another example, with one of the first and second actuators actuated, the other of the first and second actuators can be configured to be actuated and thereby override a direction of the impacting caused by the actuation of the one of the first and second actuators.

For still another example, at least one of the first and second actuators can include a tactile element configured to distinguish the first and second actuators from one another by feel. Further, each of the first and second actuators can include a tactile element, or only one of the first and second actuators includes a tactile element.

For another example, the surgical device can include a motor operatively coupled to the first and second actuators, the actuation of the first actuator can be configured to cause a first Hall effect sensor to output a first voltage that triggers the motor to move in a first direction, and the actuation of the second actuator can be configured to cause a second Hall effect sensor to output a second voltage that triggers the motor to move in a second direction that is opposite to the first direction. Further, the first actuator can include a first magnet configured to interact with the first Hall effect sensor in response to the actuation of the first actuator, and the second actuator can include a second magnet configured to interact with the second Hall effect sensor in response to the actuation of the second actuator; the surgical device can include a control board operatively coupled to the motor, the first Hall effect sensor, and the second Hall effect sensor, and the control board can be configured to provide a control signal to the motor based on the control board receiving either the first voltage or the second voltage; and/or the motor can be disposed within a body of the handpiece.

For another example, the surgical device can include a motor operatively coupled to the first and second actuators, the actuation of the first actuator can be configured to control movement of the motor in a first direction, and the actuation of the second actuator can be configured to control movement of the motor in a second direction that is opposite to the first direction. Further, the motor can be disposed within a body of the handpiece, and/or the first actuator can include a first magnet, the second actuator can include a second magnet, the handpiece can include a first Hall effect sensor operatively coupled to the motor and a second Hall effect sensor operatively coupled to the motor, the actuation of the first actuator can be configured to cause the first magnet to move relative to the first Hall effect sensor and thereby trigger the motor to move in the first direction, and the actuation of the second actuator can be configured to cause the second magnet to move relative to the second Hall effect sensor and thereby trigger the motor to move in the second direction. Further, the surgical device can also include a control board operatively coupled to the motor, the first Hall effect sensor, and the second Hall effect sensor, the control board can be configured to provide a first control signal to the motor based on a signal received from the first Hall effect signal to cause the motor to move in the first direction, and the control board can be configured to provide a second control signal to the motor based on a signal received from the second Hall effect signal to cause the motor to move in the second direction.

For still another example, the first and second actuators can each include a depressible trigger.

For another example, the first actuator can include a first element, and the second actuator can include a second element that is pivotally coupled to the first element at a pivot point.

For another example, the surgical device can also include the handpiece and a surgical implement configured to couple to the handpiece; with the surgical implement coupled to the handpiece, the actuation of the first actuator can be configured to cause the surgical implement to be driven in the forward direction; and, with the surgical implement coupled to the handpiece, the actuation of the second actuator can be configured to cause the surgical implement to be driven in the rearward direction. Further, the surgical device can also include an adapter configured to releasably couple to the handpiece and configured to couple the surgical implement to the handpiece, and/or the surgical implement includes a chisel or a broach. Further, the surgical implement can be configured to releasably couple to the adapter, or the surgical implement can be non-releasably coupled to the adapter.

In another embodiment, a surgical device includes a handpiece configured to be held by a hand of a user. The handpiece is configured to drive impacting of bone. The handpiece includes an actuator configured to be hand-actuated and thereby cause the impacting to be in one of a forward direction toward the bone and a rearward direction away from the bone, and a mode selector configured to be receive a user input that selects whether the impacting caused by the actuation of the actuator is in the forward direction or the rearward direction.

The surgical device can have any number of variations. For example, the handpiece can include a body and a handle extending from the body, the handle can be configured to be held by the hand, one of the actuator and the mode selector can be on the handle, and the other of the actuator and the mode selector can be on the body.

For another example, at least one of the actuator and the mode selector can include a tactile element configured to distinguish the actuator and the mode selector from one another by feel. Further, each of the actuator and the mode selector can include a tactile element, or only one of the actuator and the mode selector can include a tactile element.

For yet another example, the surgical device can also include a motor operatively coupled to the actuator, the actuation of the actuator can be configured to trigger the motor to move, a first user input to the mode selector selecting a first mode of operation can correspond to the motor moving in a first direction configured to cause the impacting to be in the forward direction toward the bone, and a second user input to the mode selector selecting a second mode of operation can correspond to the motor moving in a second direction configured to cause the impacting to be in the rearward direction toward the bone, the second direction being opposite to the first direction. Further, the motor can be disposed within a body of the handpiece; and/or the surgical device can also include a control board operatively coupled to the motor, the actuator, and the mode selector, and the control board can be configured to provide a control signal to the motor based on the selected mode of operation.

For still another example, the surgical device can include the handpiece and a surgical implement configured to couple to the handpiece, and, with the surgical implement coupled to the handpiece, the actuation of the actuator can be configured to cause the surgical implement to be driven in one of the forward direction or the rearward direction based on the user input to the mode selector.

In another aspect, a surgical method is provided that in one embodiment includes actuating a first actuator of a surgical device and thereby causing a surgical implement operatively coupled to the first actuator to move forward relative to bone, and actuating a second actuator of the surgical device and thereby causing the surgical implement operatively coupled to the second actuator to move rearward relative to the bone. The surgical device includes a handpiece configured to be held by a hand and configured to drive impacting of bone. The handpiece includes the first actuator configured to be hand-actuated and thereby cause the impacting to be in a forward direction toward the bone, and the second actuator configured to be hand-actuated and thereby cause the impacting to be in a rearward direction away from the bone. The first and second actuators are configured to be actuated independently of one another.

The method can vary in any number of ways. For example, the second actuator can be actuated after the first actuator has been actuated.

For another example, the second actuator can be actuated with the first actuator being actuated, and the actuation of the second actuator can override the actuation of the first actuator such that the surgical implement moves rearward relative to the bone. Further, the surgical method can also include ceasing actuation of the second actuator with the first actuator still being actuated such that the surgical implement moves forward relative to the bone.

In another embodiment, a surgical method includes providing an input to a mode selector of a surgical device and thereby selecting whether the impacting caused by the actuation of am actuator of the surgical device is in the forward direction or the rearward direction, and actuating the actuator and thereby causing a surgical implement operatively coupled to the actuator to move either forward or rearward relative to the bone based on the selection. The surgical device includes a handpiece configured to be held by a hand of a user. The handpiece is configured to drive impacting of bone. The handpiece includes the actuator configured to be hand-actuated and thereby cause the impacting to be in one of a forward direction toward the bone and a rearward direction away from the bone, and the mode selector configured to be receive a user input that selects whether the impacting caused by the actuation of the actuator is in the forward direction or the rearward direction.

The surgical method can have any number of variations. For example, the surgical device can also include a motor operatively coupled to the actuator, the actuation of the actuator can be configured to trigger the motor to move, a first user input to the mode selector selecting a first mode of operation can correspond to the motor moving in a first direction configured to cause the impacting to be in the forward direction toward the bone, and a second user input to the mode selector selecting a second mode of operation can correspond to the motor moving in a second direction configured to cause the impacting to be in the rearward direction toward the bone, the second direction being opposite to the first direction. Further, the motor can be disposed within a body of the handpiece; and/or the surgical device can also include a control board operatively coupled to the motor, the actuator, and the mode selector, and the control board can be configured to provide a control signal to the motor based on the selected mode of operation.

BRIEF DESCRIPTION OF DRAWINGS

This disclosure will be more fully understood from the following detailed description taken in conjunction with the accompanying drawings, in which.

DETAILED DESCRIPTION

Figure 1:
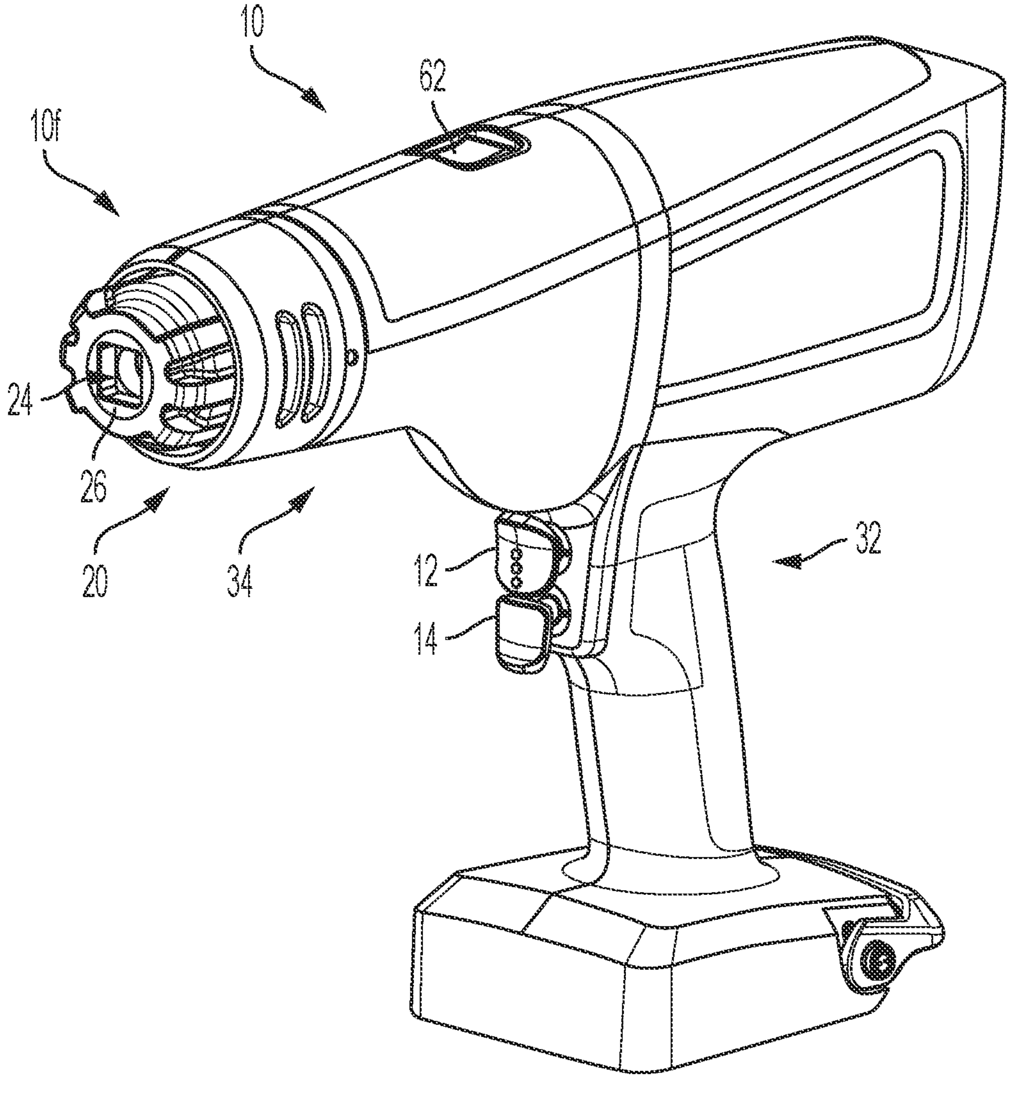
FIG. 1 is a perspective view of one embodiment of a surgical impacting tool handpiece.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

In general, devices, systems, and methods for controlling impact direction of surgical impacting tools are provided. In an exemplary implementation, a handpiece of a surgical impacting tool includes at least one actuator configured to be actuated by a user to control a direction of impacting. The surgical impacting tool handpiece, such as a handpiece of an orthopedic impactor, is configured to drive impacting of the surgical implement relative to bone. The handpiece is configured to be held by one or two hands of a user. The at least one actuator is configured to be manually actuated by hand. A user holding the handpiece can thus actuate the actuator using the one hand (or using one or both of the two hands) holding the handpiece without having to change their grip on the handpiece and/or without having to otherwise move the handpiece relative to the target bone. Not moving the handpiece relative to the target bone may improve impact responsiveness time and/or may help ensure that the impacting occurs at a desired location on the bone and that one or more structures adjacent to the bone are not accidentally impacted.

Some traditional surgical impacting tools are configured to control a direction of impacting based on a biasing force applied to the tool by a user, e.g., by the user pushing the tool to select forward impacting or pulling the tool to select reverse impacting. Thus, if a user desires to change from forward impacting to reverse impacting, or vice versa, the user must change their grip on the tool and/or move the tool relative to the target bone.

Figure 2:
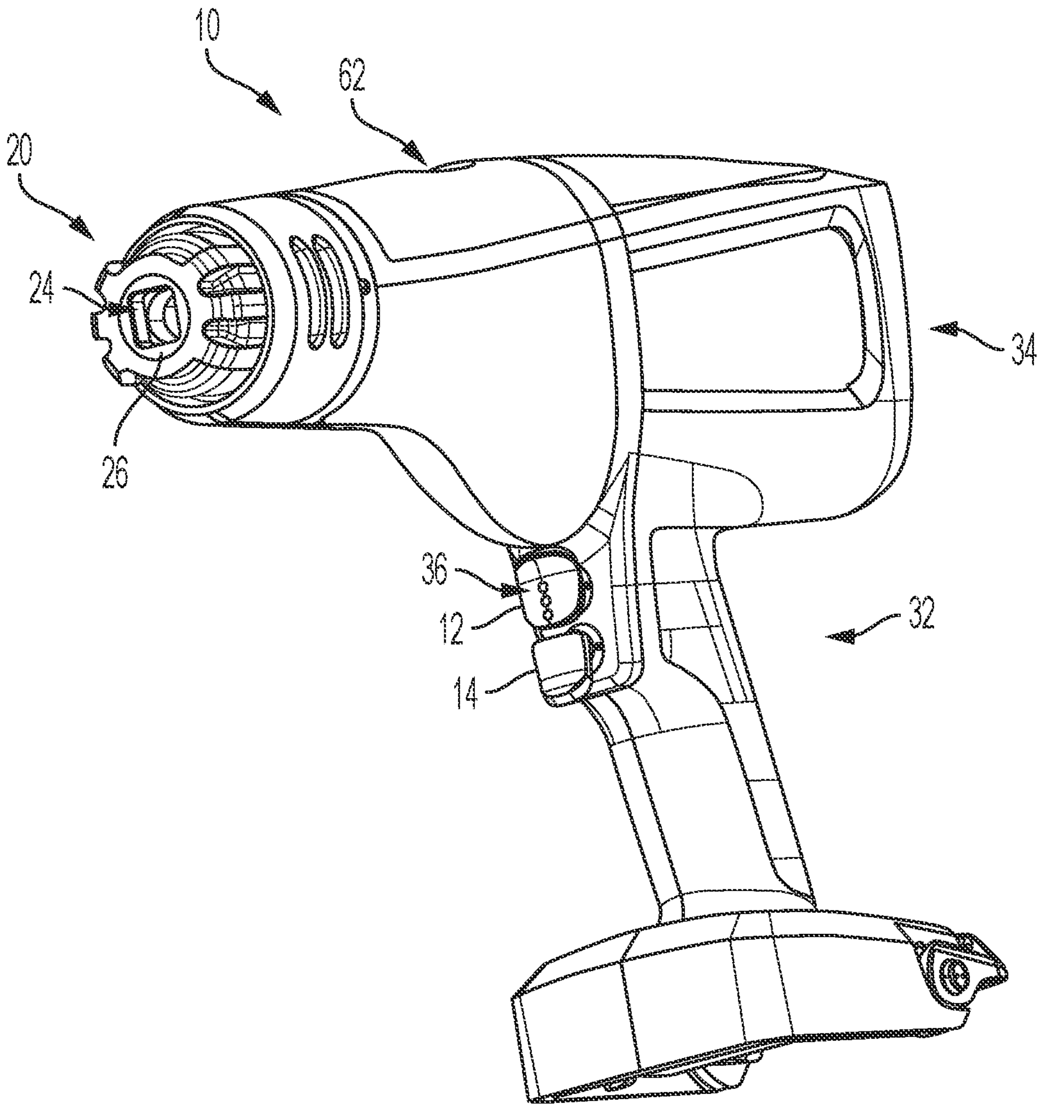
FIG. 2 is a another perspective view of the surgical impacting tool handpiece of FIG. 1.
Figure 3:
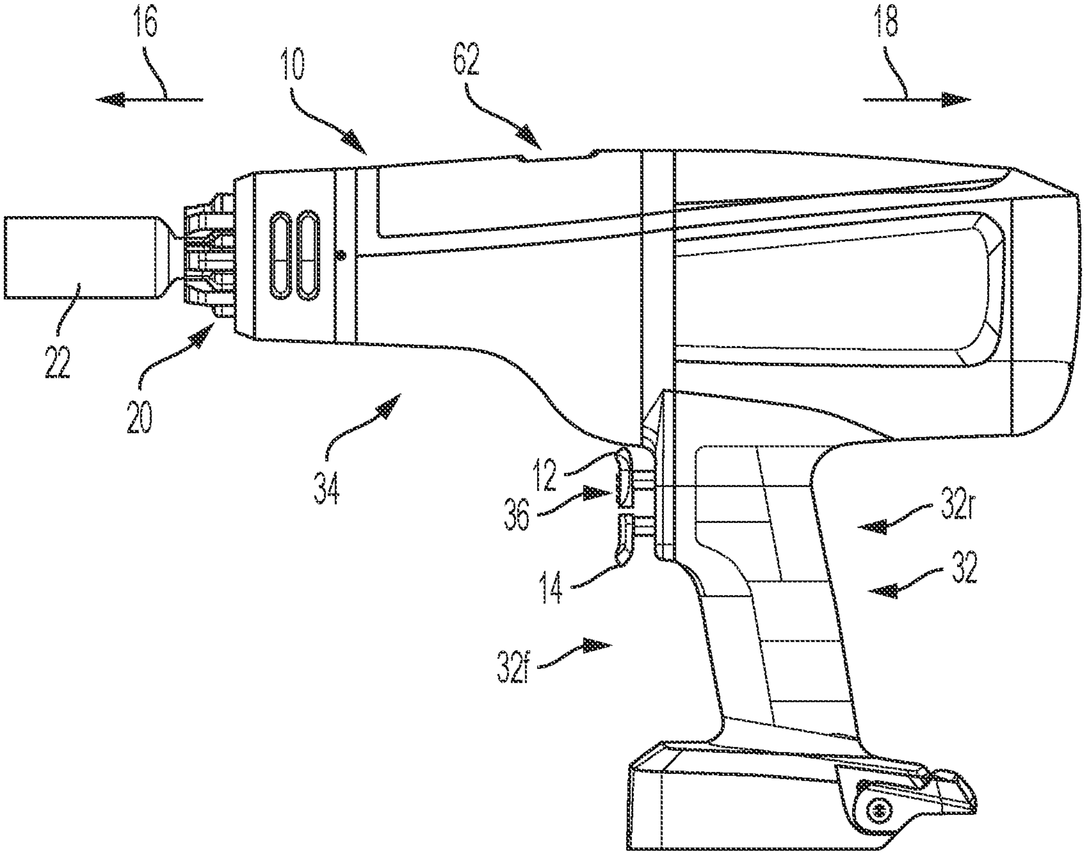
FIG. 3 is a left side view of the surgical impacting tool handpiece of FIG. 1.

FIGS. 1-3 illustrate one embodiment of a surgical impacting tool handpiece 10 configured to allow control of impact direction. The handpiece 10 is a handpiece of an orthopedic impactor in this illustrated embodiment, but as mentioned above, the surgical impacting tool can be another type of surgical impacting tool.

The handpiece 10 includes first and second actuators 12, 14. As discussed further below, the first actuator 12 is configured to be actuated to cause impacting in a forward direction 16, and the second actuator 14 is configured to be actuated to cause impacting in a rearward direction 18. To provide forward impacting, the handpiece 10 is configured to provide a forward force for impacting bone in the forward direction 16, and to provide rearward impacting, the handpiece 10 is configured to provide a rearward force for impacting bone in the rearward direction 18. The handpiece 10 is thus configured to provide bidirectional impacting since impacting can be provided in two directions (forward and rearward). The handpiece 10 is also configured to selectively provide forward and rearward impacting, depending on which one of the first and second actuators 12, 14 is actuated. In some embodiments, as discussed further below, both of the first and second actuators 12, 14 may be actuated, with the one of the first and second actuators 12, 14 actuated second being the actuator 12, 14 that controls whether forward impacting or rearward impacting is provided.

Figure 4:
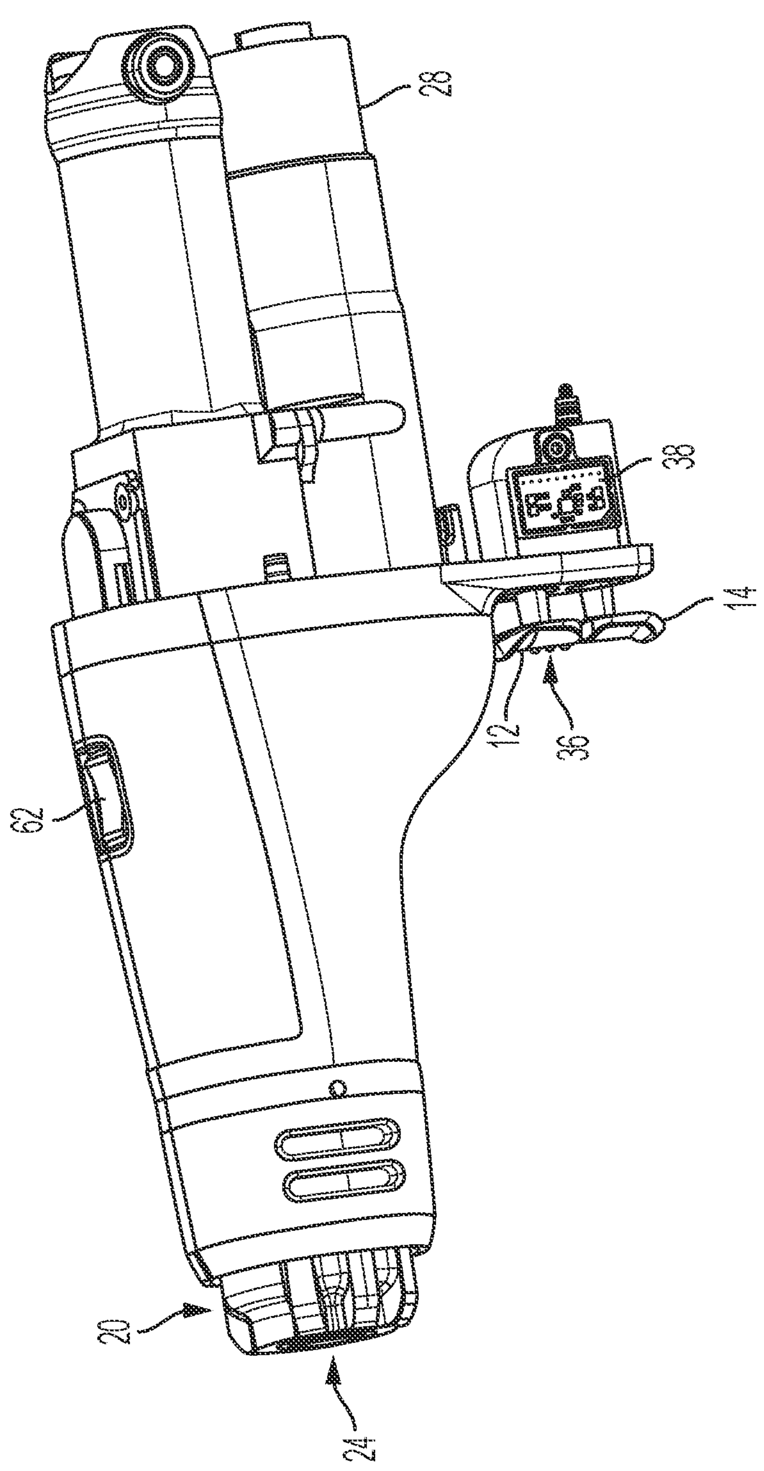
FIG. 4 is a perspective view of a portion of the surgical impacting tool handpiece of FIG. 1.
Figure 5:
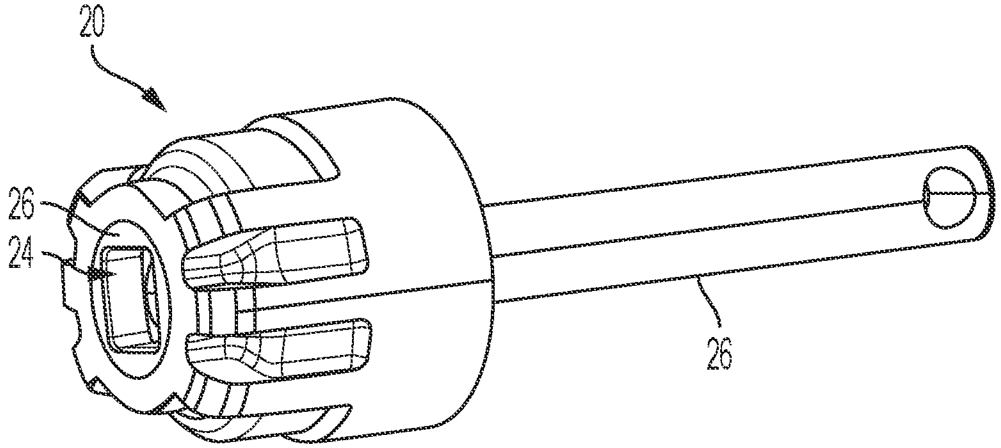
FIG. 5 is a perspective view of an anvil of the surgical impacting tool handpiece of FIG. 1.

The surgical impacting tool handpiece 10 includes a locking assembly 20 configured to be releasably coupled to an adapter. FIG. 3 shows the handpiece 10 releasably coupled to one embodiment of an adapter 22 via the locking assembly 20. The locking assembly 20 is also shown in FIG. 4 and is shown as a standalone element in FIG. 5. The adapter 22 is configured to be coupled (releasably or non-releasably) to a surgical implement (not shown) configured to impact bone. With the surgical implement coupled to the handpiece 10 via the adapter, the handpiece 10 is configured to providing a force to the surgical implement, via the adapter, to drive impacting of the surgical implement relative to bone. Whether the force is a forward force, to drive forward impacting, or a rearward force, to drive rearward impacting, depends on whether the first actuator 12 or the second actuator 14 is actuated or, in some embodiments, which one of the actuated first and second actuators 12, 14 was last actuated.

The locking assembly 20 is located at a distal or forward end 10*f* of the handpiece 10. The adapter 22 releasably coupled to the locking assembly 20 can therefore extend distally from the handpiece 10, as shown in FIG. 3. In general, the locking assembly 20 is configured to move between a locked configuration, in which the locking assembly 20 is releasably attached to an adapter, and an unlocked configuration, in which the locking assembly 20 is not releasably attached to an adapter.

The locking assembly 20 can have a variety of configurations. As shown in this illustrated embodiment, the locking assembly 20 includes a cavity 24 configured to seat a rearward portion of the adapter 22 (or other adapter) therein. The cavity 24 is located at a forward or distal end of the locking assembly 20 and thus at the forward end 10*f* of the handpiece 10. The cavity 24 is formed in a base 26 of the locking assembly 20. A forward or distal portion of the base 26 has the cavity 24 formed therein such that the cavity 24 is accessible at the forward end of the locking assembly 20.

As shown in this illustrated embodiment, the base 26 can be an anvil of the handpiece 10. The anvil 26 is configured to impact a first surface of the surgical impacting tool, such as a first surface of the adapter 20 releasably coupled to the handpiece 10, to provide forward impacting and to impact a second surface of the surgical impacting tool, such as a second surface of the adapter 20 releasably coupled to the handpiece 10, to provide rearward impacting.

Various exemplary embodiments of adapters, surgical implements, and locking assemblies for surgical impacting tools are further described, for example, in U.S. patent application Ser. No. 17/319,700 entitled "Surgical Impacting Tool Interfaces" filed May 13, 2021, U.S. Prov. Pat. App. Ser. No. 63/425,911 entitled "Surgical Impacting Tool Couplings" filed Nov. 16, 2022, U.S. Pat. Pub. No. 2013/0161050 entitled "Electric Motor Driven Tool For Orthopedic Impacting" published Jun. 27, 2013, and U.S. Pat. No. 10,912,597 entitled "Orthopedic Adapter For An Electric Impacting Tool" issued Feb. 9, 2021, which are hereby each incorporated by reference in their entirety.

Figure 6:
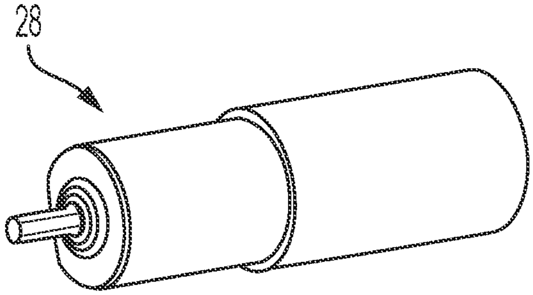
FIG. 6 is a perspective view of a motor of the surgical impacting tool handpiece of FIG. 1.

The anvil 26 is configured to be operably coupled to a drive mechanism of the handpiece 10 to allow the drive mechanism to provide a longitudinally directed force (forward or rearward) to the anvil 26 to drive impacting. The drive mechanism can have a variety of configurations. As in this illustrated embodiment, the drive mechanism can include a motor 28 configured to drive impacting. The motor 28 is an electric motor in this illustrated embodiment. FIG. 6 shows the motor 28 as a standalone element. Various embodiments of drive mechanisms are further described, for example, in U.S. Pat. Pub. No. 2013/0161050 entitled "Electric Motor Driven Tool For Orthopedic Impacting" published Jun. 27, 2013, U.S. Pat. No. 10,912,597 entitled "Orthopedic Adapter For An Electric Impacting Tool" issued Feb. 9, 2021, U.S. Pat. No. 11,013,503 entitled "Orthopedic Device Delivering A Controlled, Repeatable Impact" issued May 25, 2021, U.S. Pat. No. 11,083,512 entitled "Orthopedic Impacting Device Delivering A Controlled, Repeatable Impact" issued Aug. 10, 2021, U.S. Pat. No. 11,134,962 entitled "Orthopedic Impacting Device Having A Launched Mass Delivering A Controlled, Repeatable & Reversible Impacting Force" issued Oct. 5, 2021, U.S. Pat. No. 8,393,409 entitled "Electric Motor Driven Tool For Orthopedic Impacting" issued Mar. 12, 2013, U.S. Pat. No. 8,936,105 entitled "Electric Motor Driven Tool For Orthopedic Impacting" issued Jan. 20, 2015, and U.S. Pat. No. 8,695,726 entitled "Electric Motor Driven Tool For Orthopedic Impacting" issued Apr. 15, 2014, which are hereby each incorporated by reference in their entirety.

The actuation of the first and second actuators 12, 14 is configured to trigger the drive mechanism to drive impacting. Thus, the actuation of the first actuator 12 is configured to trigger the motor 28 to drive forward impacting, and the actuation of the second actuator 14 is configured to trigger the motor 28 to drive rearward impacting.

The handpiece 10 includes a control board 38 (see FIGS. 4 and 7) operatively coupled to the motor 28, the first actuator 12, and the second actuator 14. The control board 38 can have a variety of configurations, such as a microprocessor, a printed circuit board (PCB), etc.

In response to actuation of an actuator 12, 14, the control board 38 is configured to provide a control signal to the motor 28 that causes the motor 28 to drive impacting. The control signal causes the motor 28 to rotate or spin in a direction based on whether the first actuator 12 or the second actuator 14 has been actuated, thereby allowing forward and rearward impacting to be selectively provided. More particularly, in response to actuation of the first actuator 12, the control board 38 is configured to provide a control signal to the motor 28 that causes the motor 28 to rotate or spin in a first direction that causes the anvil 26 to impact the first surface to provide a forward force for forward impacting. In response to actuation of the second actuator 14, the control board 38 is configured to provide a control signal to the motor 28 that causes the motor 28 to rotate or spin in a second direction that causes the anvil 26 to impact the second surface to provide a rearward force for rearward impacting. The second direction of motor 28 rotation or spinning is opposite to the first direction.

The first actuator 12 includes a first magnet 40 configured to interact with a first Hall effect sensor 42 of the control board 38. Actuation of the first actuator 12 is configured to cause the first magnet 40 to move toward the control board 38 and thus toward the first Hall effect sensor 42. An electromagnetic field sensed by the first Hall effect sensor 42 thus changes, thereby triggering the control board 38 to provide a control signal to the motor 28 to drive forward impacting.

Figure 7:
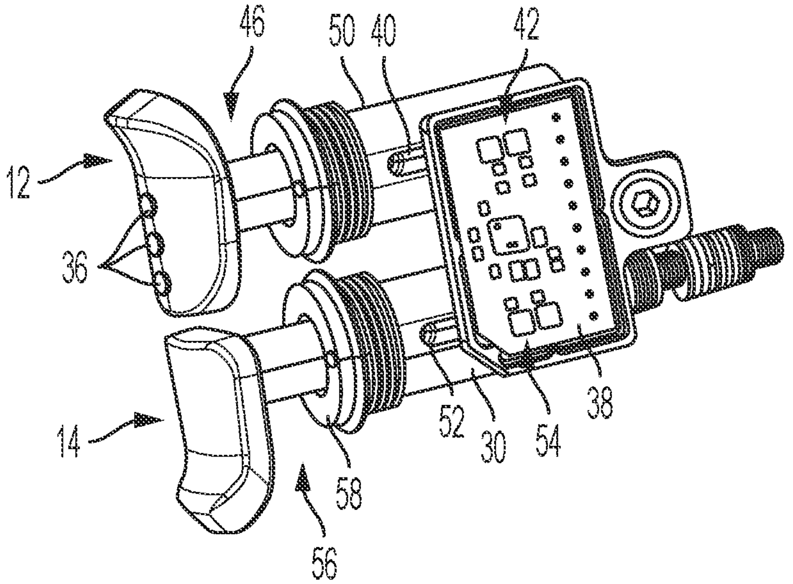
FIG. 7 is a perspective view of another portion of the surgical impacting tool handpiece of FIG. 1.
Figure 8:
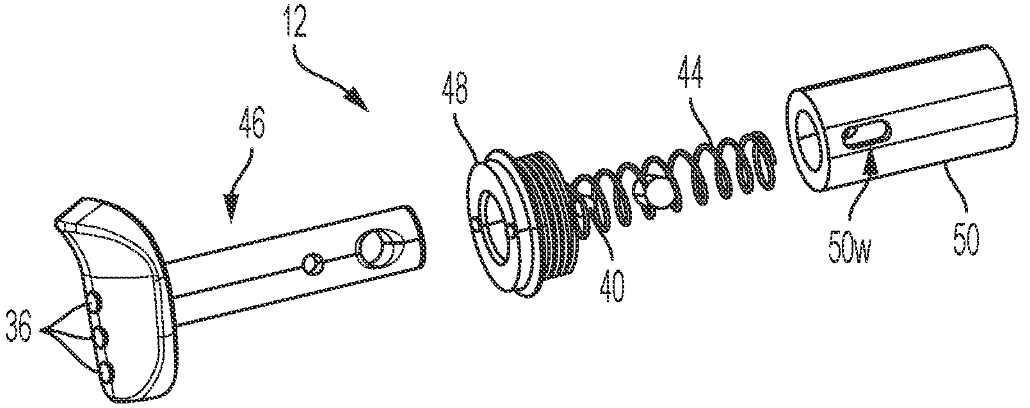
FIG. 8 is a partially exploded view of a first actuator of the surgical impacting tool handpiece of FIG. 1.

More particularly, the first actuator 12 includes a first spring 44 that biases the first magnet 40 to a first, outward position, which is shown in FIG. 7. Actuation of the first actuator 12 overcomes the first spring 44 biasing force by a first trigger 46 of the first actuator 12 being pushed inwardly, e.g., toward the handle 32 and toward a first nut 48 of the first actuator 12. The first nut 48 is configured as a stop member that stops inward movement of the first trigger 46 after the first trigger 46 has moved inwardly a certain distance. The first magnet 40 is in a fixed position relative to the first trigger 46. The inward movement of the first trigger 46 thus causes inward movement of the first magnet 40 such that the first magnet 40 moves closer to the first Hall effect sensor 42. The first nut 48 stopping the first trigger's inward movement, and thus also stopping the first magnet's inward movement, with the first magnet 40 in a second, inward position is configured to allow the electromagnetic field sensed by the first Hall effect sensor 42 to be at a certain, known value that triggers the control board 38 to provide the control signal to the motor 28 to causes forward impacting. In response to release of the first actuator 12, e.g., release of the first trigger 46, force provided by the first spring 44 urges the first trigger 46, and thus the first magnet 40, radially outward and back to the first, outward position.

The first actuator 12 also includes a first sleeve 50 that houses therein the first magnet 40 and the first spring 44 and in which the first trigger 46 is configured to move radially inward and outward. The first sleeve 50 has a longitudinal opening or window 50*w* formed therethrough. The opening or window 50*w* is located along the first magnet's inward-outward longitudinal path of movement and is configured to facilitate interaction of the first magnet 40 with the first Hall effect sensor 42.

The second actuator 14 is configured and used similar to the first actuator 12 and includes a second magnet 52 configured to interact with a second Hall effect sensor 54 of the control board 38; a second spring (obscured in the figures); a second trigger 56; a second nut 58; and a second sleeve 60.

In some situations, a user may want to perform feathering with a surgical impacting tool in which reverse impacting quickly occurs when forwarding impacting is being provided by the tool, or vice versa. Having to stop actuating the surgical impacting tool handpiece's first actuator before actuating the second handpiece's actuator takes time and can be awkward for a user.

In some embodiments, actuation of one of the first and second actuators while the other of the first and second actuators is already actuated is configured to override the first, earlier actuation. In other words, if the second actuator for reverse impacting is actuated with the first actuator for forward impacting already actuated, the surgical impacting tool is configured to switch to reverse impacting for as long as the second actuator is also being actuated. Feathering may thus be performed without a user holding the handpiece having to stop actuating the first actuator such that forward impacting can immediately precede and immediately following the reverse impacting triggered by the second actuator's actuation. Similarly, if the first actuator for forward impacting is actuated with the second actuator for reverse impacting already actuated, the surgical impacting tool is configured to switch to forward impacting for as long as the second actuator is also being actuated. Feathering may thus be performed without a user holding the handpiece having to stop actuating the second actuator such that reverse impacting can immediately precede and immediately following the forward impacting triggered by the first actuator's actuation.

In other embodiments, only one of a surgical impacting tool handpiece's first and second actuators can be configured to be actuated at a time. Such a configuration may help ensure that an unintended direction of impacting does not occur, e.g., by an unintended actuation of one of the first and second actuators while the other of the first and second actuators is already actuated.

The first and second actuators 12, 14 are located on the handpiece 10 at locations configured to make the first and second actuators 12, 14 easy to actuate by hand by a user holding the handpiece 10. The actuators 12, 14 in this illustrated embodiment are each located on a handle 32 of the handpiece 10. The handle 32 is configured to be held by a user's hand. The first and second actuators 12, 14 being located on the handle 32 can thus conveniently position the first and second actuators 12, 14 for manual manipulation by the user's thumb and/or one or more fingers of the user's hand since the user's hand is already at the handle 32.

As shown in FIGS. 1-3, the actuators 12, 14 are each located on a distal or forward side 32*f* of the handle 32. Thus, when a user is holding the handle 32 with their palm on or facing a rear side 32*r* of the handle 32, the user's fingers will wrap around the handle 32 toward the forward side 32*f*. The user can thus use one or more of their fingers to actuate the first and second actuators 12, 14 without having to alter their hand grip of the handle 32. Some users may prefer to actuate the first and second actuators 12, 14 with a same finger (or thumb), moving the finger (or thumb) as needed to actuate the desired actuator 12, 14. Other users may prefer to actuate each of the first and second actuators 12, 14 with a different finger or thumb, e.g., the upper, first actuator 12 with their pointer finger and the lower, second actuator 14 with their middle finger.

The handpiece 10 may not always be held with the user's palm on or facing a rear side 32*r* of the handle 32. One or more factors such as different patient positions during performance of a surgical procedure, use of the handpiece 10 with respect to different parts of a patient's body, and different medical professional preferences may make an opposite handhold of the handle 32 preferable. In such situations, the user's handhold can be in reverse with the user's palm on or facing the forward side 32*f* of the handle 32 with the user's fingers wrapping around the handle 32 toward the rear side 32*r*. The first and second actuators 12, 14 on the forward side 32*f* of the handle 32 may thus be difficult for the user to actuate as desired without having to readjust hand position on the handle 32 or use another hand to actuate the first and second actuators 12, 14.

Figure 9:
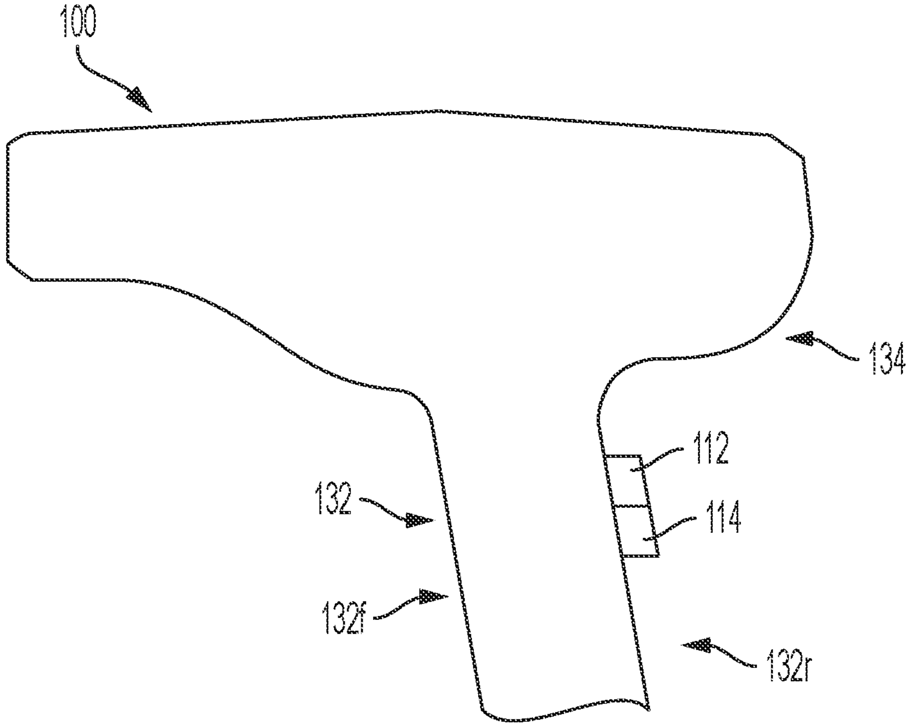
FIG. 9 is a left side view of another embodiment of a surgical impacting tool handpiece.

FIG. 9 illustrates an embodiment of a surgical impacting tool handpiece 100 including first and second actuators 112, 114 on a rear side 132*r* of a handle 132 of the handpiece 100. The handpiece 100 is otherwise configured and used similar to the handpiece 10 of FIGS. 1-3. When a user is holding the handpiece 100 with their palm on or facing a forward side 132*f* of the handle 132 with the user's fingers wrapped around the handle 132 toward the rear side 132*r*, the first and second actuators 112, 114 will be conveniently located for the user to use one or more of their fingers (or thumb) to actuate the first and second actuators 112, 114 without having to alter their hand grip of the handle 132.

In some situations, a surgical impacting tool handpiece, such as the handpiece 10 of FIGS. 1-3 or the handpiece 100 of FIG. 9, will be held in a generally upright orientation in which the handle located is below a body of the handpiece. FIGS. 1-3 each show the handpiece 10 in a generally upright orientation in which the handle 32 is located below a body 34 of the handpiece 10. FIG. 9 shows the handpiece 100 in a generally upright orientation in which the handle 132 is located below a body 134 of the handpiece 100.

In other situations, a surgical impacting tool handpiece, such as the handpiece 10 of FIGS. 1-3 or the handpiece 100 of FIG. 9, will not be held in a generally upright orientation due to one or more factors such as different patient positions during performance of a surgical procedure, use of the handpiece with respect to different parts of a patient's body, and different medical professional preferences. In such situations, the handpiece may be held in a generally inverted orientation in which the handle located is above a body of the handpiece. A user may be able to hold the handle with one hand while the handpiece is in the generally inverted orientation such that the handpiece's first and second actuators each located on either a rear side or a forward side of the handpiece may be able to be actuated by the user. However, surgical impacting tool handpieces are typically heavy enough, e.g., due to relatively heavy components such as a motor, a power source, etc., that holding the handpiece with one hand while the handpiece is in a generally inverted orientation may be too unsteady for impacting and/or too uncomfortable to hold. A user may thus use two hands to hold a surgical impacting tool handpiece in a generally inverted orientation. Neither of the hands may be holding the handle as discussed above with respect to the generally upright orientation of the handpiece. Instead, one hand may be holding the handpiece's body while the other hand supports the handle to keep the handpiece in the generally inverted orientation. In such situations, one or both of the first and second actuators being located on the body of the handpiece may make the first and second actuators easy to actuate with the handpiece in the generally inverted orientation.

Figure 10:
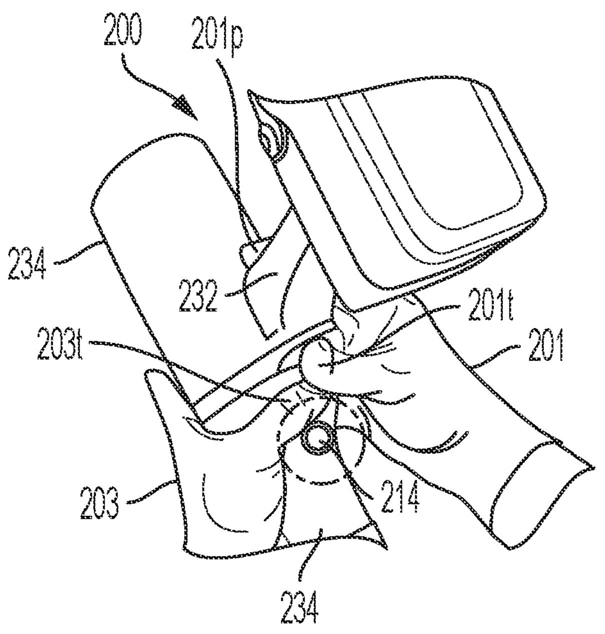
FIG. 10 is a perspective, partial view of another embodiment of a surgical impacting tool handpiece being held by a user.

FIG. 10 illustrates an embodiment of a surgical impacting tool handpiece 200 being held by a user in a generally inverted orientation. The handpiece 200 is configured and used similar to the handpiece 10 of FIGS. 1-3. A first hand 201 of the user is holding a handle 232 of the handpiece 200, and a second hand 203 of the user is holding a body 234 of the handpiece 200. A pointer finger 201*p* of the user's first hand 201 is shown resting on a first actuator of the handpiece 200. The first actuator is on a rearward side of the handle 232 and is obscured in the view of FIG. 10. A thumb 203*t* of the user's second hand 203 is shown positioned near a second actuator 214 of the handpiece 200. The second actuator 214 is located on an underside of the body 234 forward of the handle 232. The first actuator and the second actuator 214 can thus each be easily actuated by the user without the user having to adjust their grip of the handpiece 200, with the first actuator being actuated by the first hand 201, e.g., by the pointer finger 201*p*, and the second actuator 214 being actuated by the second hand 203, e.g., by the thumb 203*t*. Some users may prefer to actuate both of the first actuator and the second actuator 214 with the first hand 201, e.g., with the pointer finger 201*f* actuating the first actuator and a thumb 201*t* of the first hand 201 actuating the second actuator 214.

In some embodiments, instead of the first actuator being located on the rearward side of the handle 232, the first actuator can be located on a forward side of the handle 232. In such embodiments, the thumb 201*t* of the user's first hand 201 may be easily positioned to actuate the first actuator with the handpiece 200 being held in a generally inverted orientation.

In some embodiments, instead of the second actuator 204 being located on the body 234 of the handpiece 200, the second actuator 214 can be located on one of the rearward and forward sides of the handle 232, and the first actuator can be located on the other of the rearward and forward sides of the handle 232. In such embodiments, with the handpiece 200 being held in a generally inverted orientation, one hand of the user may be able to actuate both the first actuator and the second actuator 204, e.g., the thumb 201*t* of the user's first hand 201 may be easily positioned to actuate one of the first actuator and the second actuator 214 and the pointer finger 201*p* of the user's first hand 201 may be easily positioned to actuate the other of the first actuator and the second actuator 214.

The first and second actuators of FIGS. 1-3, 9, and 10 are in a fixed position relative to their respective handpieces 10, 100, 200. In other embodiments, first and second actuators of a surgical impacting tool handpiece can be configured to be selectively repositioned by a user relative to the handpiece. The positions of the first and second actuators being selectable by a user may allow the user to position the first and second actuators in a convenient location for how the user intends to hold the handpiece. Such a handpiece may be more versatile than a handpiece having first and second actuators at fixed positions.

Figure 11:
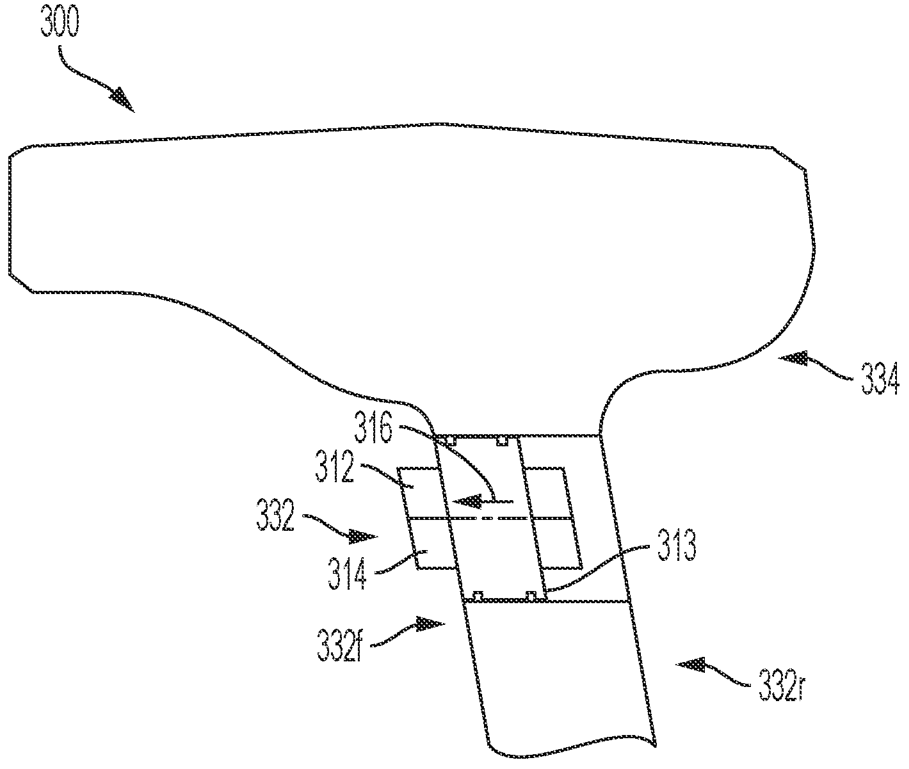
FIG. 11 is a left side view of yet another embodiment of a surgical impacting tool handpiece with first and second actuators in a forward position.
Figure 12:
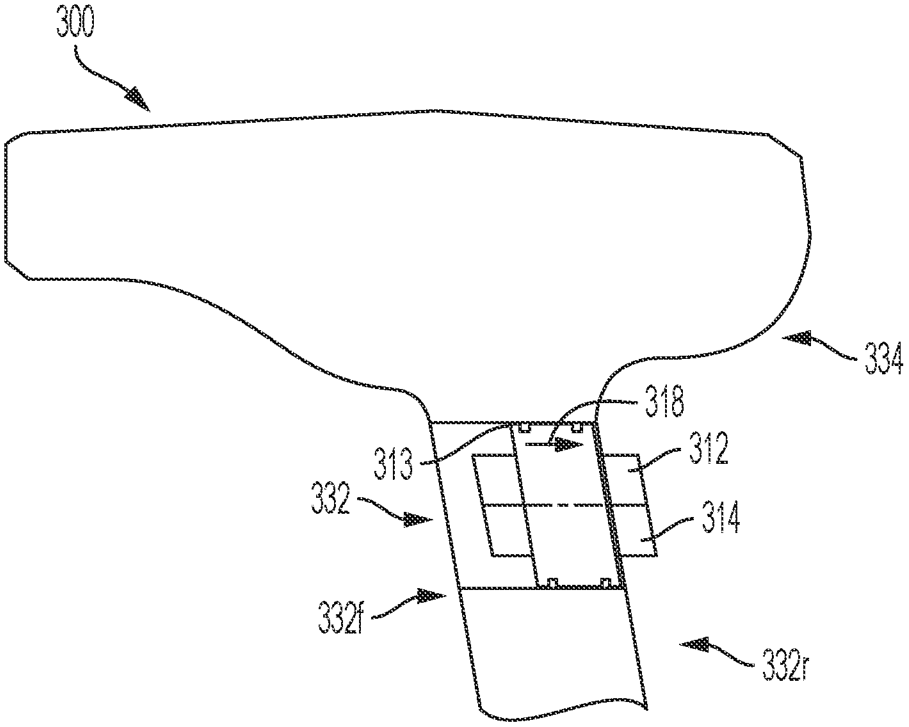
FIG. 12 is a left side view of the surgical impacting tool handpiece of FIG. 11 with the first and second actuators in a rearward position.
Figure 13:
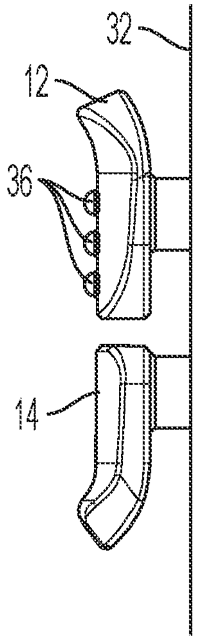
FIG. 13 is a left side view of first and second actuators and a portion of a handle of the surgical impacting tool handpiece of FIG. 1.

FIGS. 11 and 12 illustrate an embodiment of a handpiece 300 including first and second actuators 312, 314 configured to be selectively repositioned relative to the handpiece 300. The handpiece 300 is otherwise configured and used similar to the handpiece 10 of FIGS. 1-3. The first and second actuators 312, 314 are configured to be movable between a forward position, shown in FIG. 11, and a rearward position, shown in FIG. 12. In the forward position, the first and second actuators 312, 314 are located on a forward side **332*f* of the handpiece's handle 332, similar to the actuators 12, 14 of FIGS. 1-3. In the rearward position, the first and second actuators 312, 314 are located on a rearward side 332*r* of the handle 332, similar to the actuators 112, 114 of FIG. 9**.

The handpiece 300 includes a slider 313 configured to be manually moved by a user relative to the handle 332 (and relative to the handpiece's body 334) to selectively position the first and second actuators 312, 314 in the forward position or the rearward position. The slider 313 is configured to slide in a forward direction 316 to position the first and second actuators 312, 314 in the forward position. The slider 313 is configured to slide in a rearward direction 318 to position the first and second actuators 312, 314 in the rearward position.

The slider 313 can include a locking mechanism configured to temporarily lock the slider 313 relative to the handle 332 (and the body 334) and thereby temporarily lock the first and second actuators 312, 314 in either the forward position or the rearward position. The locking mechanism can have a variety of configurations. For example, the locking mechanism can include a mating element (e.g., one or more depressible spring pins) configured to releasably engage a mating feature (e.g., one or more holes) of the handle 332. For another example, the locking mechanism can include a mating feature (e.g., one or more holes) configured to releasably engage a mating element (e.g., one or more depressible spring pins) of the handle 332. For yet another example, the locking mechanism can include a latch configured to be manually engaged by the user to temporarily latch the slider 332 to the handle 332 with the first and second actuators 312, 314 in either the forward position or the rearward position.

In embodiments in which the first and second actuators are located on a same side of the handpiece's handle, the first and second actuators can be in a vertical, up-down orientation relative to one another, as shown for example in FIGS. 1-3 and 13 showing the first and second actuators 12, 14 of the handpiece 10, in FIG. 9 showing the first and second actuators 112, 114 of the handpiece 100, and in FIGS. 11 and 12 showing the first and second actuators 312, 314 of the handpiece 300. The first actuator configured to be actuated to cause impacting in the forward direction is located vertically above the second actuator that is configured to be actuated to cause impacting in a rearward direction in the embodiment of FIGS. 1-3, in the embodiment of FIG. 9, and in the embodiment of FIGS. 11 and 12. The actuator for forwarding impacting being the upper actuator located vertically above the lower actuator for rearward impacting may be an intuitive arrangement for users since "upper" or "above" tends to indicate forward while "lower" or "under" tends to indicate rearward. However, in other embodiments, the first actuator configured to be actuated to cause impacting in the forward direction can be located vertically below the second actuator configured to be actuated to cause impacting in a rearward direction.

In other embodiments, first and second actuators located on a same side of the handpiece's handle can be in a horizontal, side-by-side orientation relative to one another.

One or both a surgical impacting tool handpiece's first and second actuators can include a tactile element configured to distinguish the actuators by feel. A user touching one or both of the first and second actuators can thus determine without visual confirmation which actuator(s) are being touched by a finger or thumb. The user can thus know before actuating an actuator which actuator is being touched, which may help ensure that the desired actuator is being actuated. Further, avoiding visual confirmation of the actuator may allow the user to maintain visual focus on other aspects of the surgical procedure being performed while still providing for accurate triggering of forward or rearward impacting.

The tactile element can have a variety of configurations. For example, the tactile element can include one or more protrusions (e.g., semi-spherical bumps, longitudinal ridges, etc.) extending outwardly from an actuator. For another example, the tactile element can include one or more depressions (e.g., semi-spherical indentations, longitudinal indentations, etc.) formed in an actuator. For yet another example, the tactile element can include a knurled or other textured surface of the actuator. For another example, the tactile element can include one or more holes (e.g., circular holes, longitudinal slits, etc.) formed in an actuator.

Referring to the handpiece 10 of FIGS. 1-3, the first actuator 12 includes a tactile element 36 in the form of a plurality of protrusions, as shown in FIGS. 1-3, 7, 8, 13, and 14. The tactile element 36 includes three protrusions in this illustrated embodiment, but another number of protrusions are possible, e.g., one, two, four, etc. The plurality of protrusions are arranged vertically in this illustrated embodiment, but a plurality of protrusions can be otherwise arranged. The vertical arrangement of the plurality of protrusions may help ensure that a user feels the tactile element on the first actuator 12 as the user's fingers slides between the vertically arranged first and second actuators 12, 14 and may help ensure that a user feels the tactile element on the first actuator 12 regardless of where the user's finger (or thumb) is located vertically along the first actuator 12. The protrusions each have a semi-spherical shape in this illustrated embodiment, but as mentioned above, other configurations are possible.

The second actuator 14 in this illustrated embodiment does not include a tactile element. However, in other embodiments, the second actuator 14 can include a tactile element. In still other embodiments, the first actuator 12 may lack a tactile element while the second actuator 14 includes a tactile element. In yet other embodiments, neither of the first and second actuators 12, 14 may include a tactile element.

A shape of each of the first and second actuators of a surgical impacting tool handpiece can be configured to distinguish the actuator by feel, in addition to or instead of the actuator including a tactile element configured to distinguish the actuator by feel. The shapes of the first and second actuators can vary.

As shown in the illustrated embodiment of FIGS. 3, 7, 8, and 13, the first actuator 12 has an upper end that bends outwardly, e.g., away from the handle 32, and the second actuator 14 has a lower end that bends outwardly, e.g., away from the handle 32. The bending shapes of the first and second actuators 12, 14 are configured to allow a user to determine by feel whether they are touching the first actuator 12 or the second actuator 14. With the first and second actuators 12, 14 being arranged vertically, the upper end of the first, upper actuator 12 bending outwardly and the lower end of the second, lower actuator 14 may help guide a user's finger sliding between the first and second actuators 12, 14 to be on the intended actuator for actuation.

Figure 14:
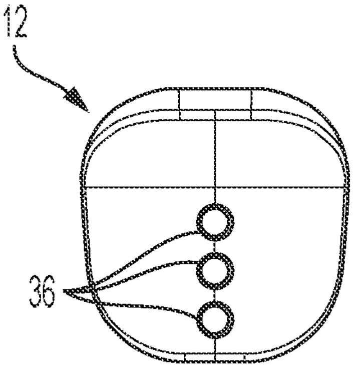
FIG. 14 is a front view of the first actuator of FIG. 13.
Figure 15:
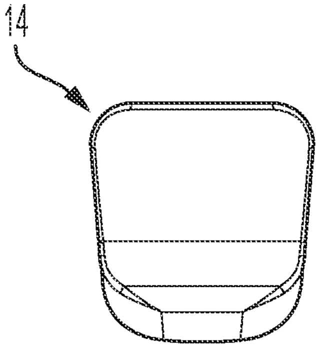
FIG. 15 is a front view of the second actuator of FIG. 13.

As shown in the illustrated embodiment of FIGS. 14 and 15, the first actuator 12 tapers radially outward in an upward direction such that the upper end of the first actuator 12 is wider than a lower end of the first actuator 12, and the second actuator 14 tapers radially outward in a downward direction such that the lower end of the second actuator 12 is wider than a upper end of the second actuator 14. With the first and second actuators 12, 14 being arranged vertically, the upper end of the first, upper actuator 12 being wider than the lower end and the lower end of the second, lower actuator 14 being wider than the upper end may help guide a user's finger sliding between the first and second actuators 12, 14 to be on the intended actuator for actuation.

Figure 16:
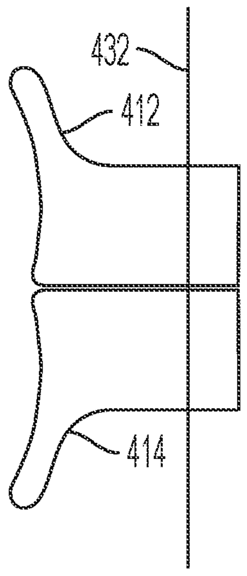
FIG. 16 is a side view of another embodiment of first and second actuators and a portion of a handle of a surgical impacting tool handpiece.

FIG. 16 illustrates another embodiment of first and second actuators 412, 414 of a surgical impacting tool handpiece. The first and second actuators 412, 414 are configured and used similar to the first and second actuators 12, 14 of the handpiece 10 of FIGS. 1-3. The first and second actuators 412, 414 in this illustrated embodiment are depressible triggers similar to the first and second actuators 12, 14 of the handpiece 10 of FIGS. 1-3. Also similar to the first and second actuators 12, 14, the first actuator 412 has an upper end that bends outwardly, e.g., away from a handle 432 of the handpiece, and the second actuator 414 has a lower end that bends outwardly, e.g., away from the handle 432.

Figure 17:
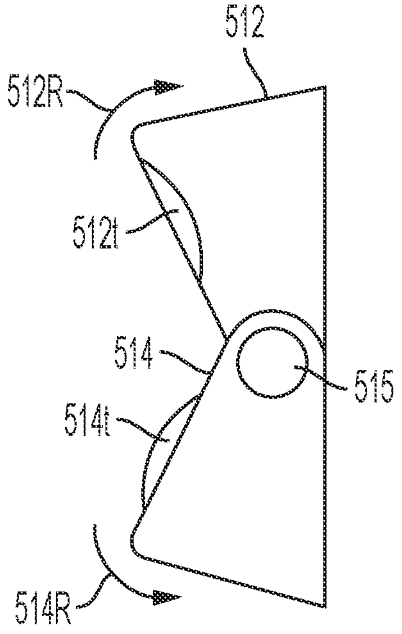
FIG. 17 is a side view of yet another embodiment of first and second actuators of a surgical impacting tool handpiece.

FIG. 17 illustrates another embodiment of first and second actuators 512, 514 of a surgical impacting tool handpiece. The first and second actuators 512, 514 are configured and used similar to the first and second actuators 12, 14 of the handpiece 10 of FIGS. 1-3. In this illustrated embodiment, the first and second actuators 512, 514 are pivotally coupled to one another at a pivot point 515. The first actuator 512 is configured to be actuated by being pushed radially inward and pivoting at the pivot point 515 as shown by arrow 512R. The second actuator 514 is configured to be actuated by being pushed radially inward and pivoting at the pivot point 515 as shown by arrow 514R.

The first and second actuators 512, 514 each include a tactile element 512*t*, 514*t*. In this illustrated embodiment, the first actuator's tactile element 512*t* includes a depression formed therein, and the second actuator's tactile element 514*t* includes a protrusion formed thereon.

Figure 18:
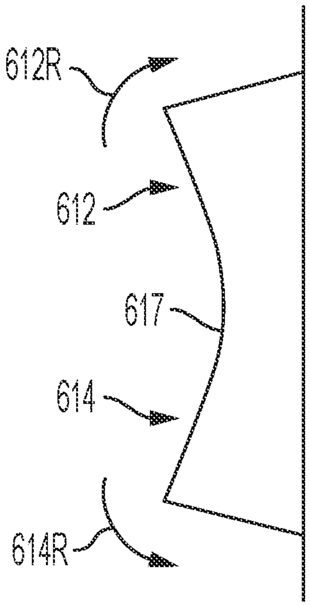
FIG. 18 is a side view of still another embodiment of first and second actuators and a portion of a handle of a surgical impacting tool handpiece.
Figure 19:
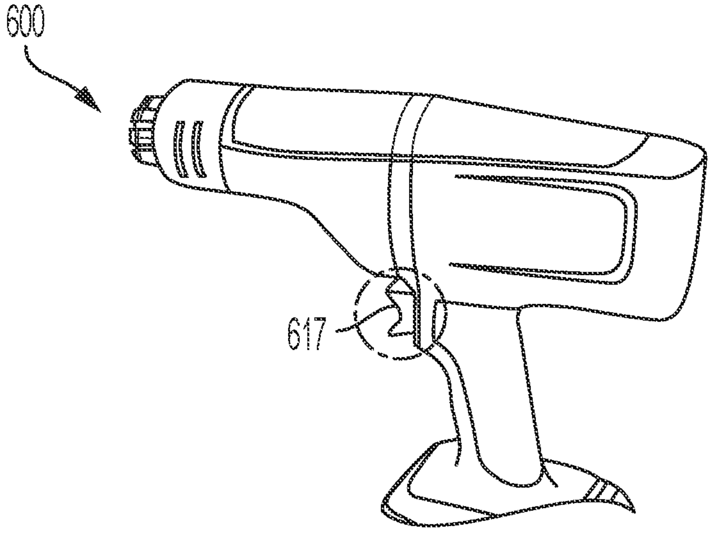
FIG. 19 is a perspective, partial view of the handpiece and first and second actuators of FIG. 18.

FIGS. 18 and 19 illustrates another embodiment of first and second actuators 612, 614 of a surgical impacting tool handpiece 600. The first and second actuators 612, 614 are configured and used similar to the first and second actuators 12, 14 of the handpiece 10 of FIGS. 1-3. In this illustrated embodiment, an upper portion of a rocker 617 defines the first actuator 612, and a lower portion of the rocker 617 defines the second actuator 614.

Other embodiments of first and second actuators include push buttons, on/off switches, limit switches, toggles switches, ring triggers, slide switches, and multi-directional switches (e.g., push and then slide, slide and then push, etc.).

In some embodiments, a surgical impacting tool handpiece can include more than two actuators. The handpiece can thus include one or more actuators configured to be actuated to provide forward impacting and one or more actuators configured to be actuated to provide rearward impacting. By having more than one actuator for forward impacting and/or more than one actuator for rearward impacting, the handpiece can provide multiple choices for a user to actuate impacting. As discussed above, handpieces may be held in different orientations, so having more than one actuator for forward impacting and/or more than one actuator for rearward impacting may help provide conveniently located actuators regardless of how the handpiece is being held.

Referring again to the handpiece 10 of FIGS. 1-3, the handpiece 10 includes a third actuator 62. The third actuator 62 in this illustrated embodiment is configured to be actuated to provide rearward impacting. In other embodiments, the third actuator 62 can be configured to be actuated to provide forward impacting.

The third actuator 62 in this illustrated embodiment is located on the body 34 of the handpiece 10. More particularly, the third actuator 62 is located on a upper side of the body 34. Such a location of the third actuator 62 may be particularly desirable for use when the handpiece 10 is being held in a generally inverted position. Other locations of the third actuator 62 are possible, such as on an underside of the body 34, similar to the second actuator 214 of FIG. 8, or on a rearward side 32*r* of the handle 32, similar to the actuators 112, 114 of FIG. 9.

The third actuator 62 in this illustrated embodiment is recessed in the handpiece 10, in particular in the body 34 of the handpiece 10. The recessed configuration of the third actuator 62 may help prevent accidental actuation of the third actuator 62, such as if a user is holding the handpiece 10 with a palm and/or one or more fingers where the third actuator 62 is located, e.g., on the upper side of the body 34.

Figure 20:
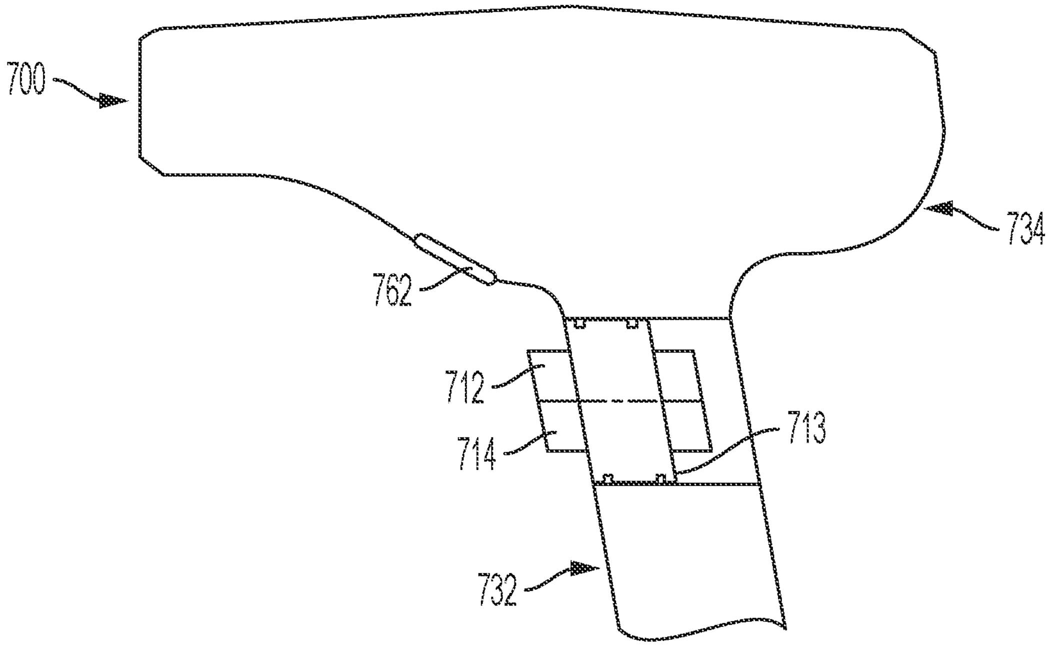
FIG. 20 is a left side, partial view of yet another embodiment of a surgical impacting tool handpiece with first and second actuators in a forward position.

FIG. 20 illustrates another embodiment of a surgical impacting tool handpiece 700 including a third actuator 762. The handpiece 700 is otherwise configured and used similar to the handpiece 300 of FIGS. 11 and 12 and includes a slider 713, a first actuator 712, and a second actuator 714 located at a handle 732 of the handpiece 700. In this illustrated embodiment, the third actuator 762 is located on a body 734 of the handpiece 700, in particular on an underside of the body 734 forward of the handle 732.

In embodiments including more than three actuators, the actuators can be in various locations as described herein.

In some embodiments, a surgical impacting tool handpiece can include a single actuator configured to selectively provide forward impacting or rearward impacting. In such embodiments, the handpiece can include a mode selector configured to select whether actuation of the actuator is configured to provide forward impacting or rearward impacting. The handpiece including a single actuator may allow a user holding the handpiece to keep a finger positioned at the actuator and not have to move that finger to effect either of forward impacting or rearward impacting. Additionally, in some surgical procedures a user may want to effect only forward impacting or to effect only rearward impacting. The handpiece including a single actuator may help ensure that the one intended direction of impacting is always provided whenever any actuator (e.g., the only actuator) is actuated.

The mode selector is configured to be operably coupled to a control board (e.g., the control board 38 of FIGS. 4 and 7, or other control board) of the handpiece. The control board is configured to provide a signal to a motor (e.g., the motor 28, or other motor) of the handpiece to rotate or spin in a direction based on a selection input to the mode selector indicating that either forward impacting or rearward impacting is desired.

The mode selector can have a variety of configurations. For example, similar to that discussed above regarding various configurations of actuators, the mode selector can be configured as depressible triggers, a two-piece selector connected at a pivot point, a rocker, push buttons, on/off switches, limit switches, toggles switches, ring triggers, slide switches, and multi-directional switches (e.g., push and then slide, slide and then push, etc.).

The mode selector and the single actuator can be at various locations on the handpiece, similar to that discussed above regarding first and second actuators.

Figure 21:
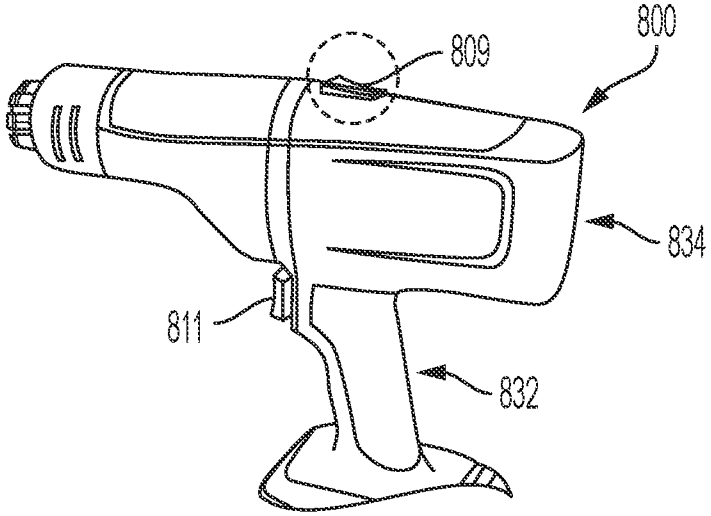
FIG. 21 is a perspective, partial view of another embodiment of a surgical impacting tool handpiece.

FIG. 21 illustrates an embodiment of a surgical impacting tool handpiece 800 including a mode selector 809 and an actuator 811. The handpiece 800 is otherwise configured and used similar to the handpiece 10 of FIGS. 1-3. In this illustrated embodiment, the mode selector 809 is on a body 834 of the handpiece 800, in particular an upper side thereof, and is configured as a switch configured to be in one position to select forward impacting and in another, opposite position to select rearward impacting. In this illustrated embodiment, the actuator 811 is on a handle 832 of the handpiece 800, in particular on a forward side of the handle 832, and is configured as a depressible trigger.

Figure 22:
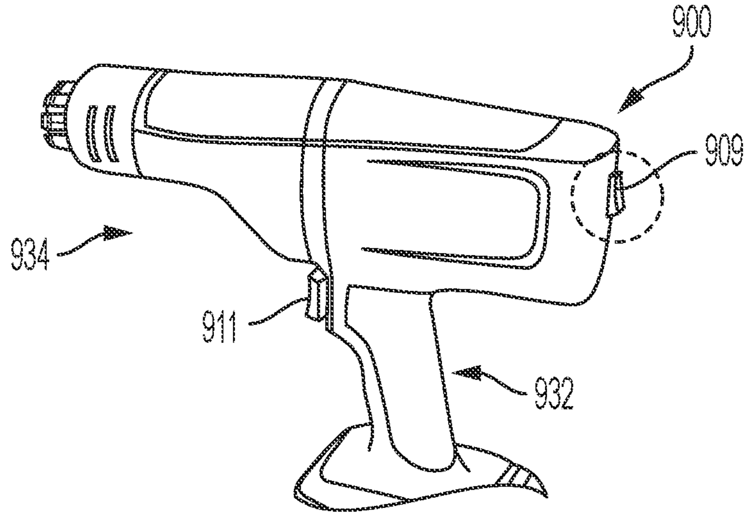
FIG. 22 is a perspective, partial view of yet another embodiment of a surgical impacting tool handpiece.

FIG. 22 illustrates an embodiment of a surgical impacting tool handpiece 900 including a mode selector 909 and an actuator 911. The handpiece 900 is otherwise configured and used similar to the handpiece 10 of FIGS. 1-3. In this illustrated embodiment, the mode selector 909 is on a body 934 of the handpiece 900, in particular a rear side thereof, and is configured as a switch configured to be in one position to select forward impacting and in another, opposite position to select rearward impacting. In this illustrated embodiment, the actuator 911 is on a handle 932 of the handpiece 900, in particular on a forward side of the handle 932, and is configured as a depressible trigger.

Figure 23:
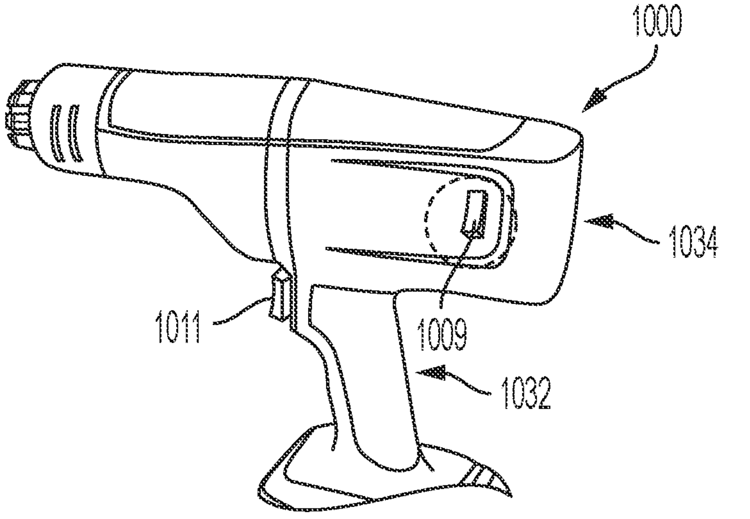
FIG. 23 is a perspective, partial view of still another embodiment of a surgical impacting tool handpiece.

FIG. 23 illustrates an embodiment of a surgical impacting tool handpiece 1000 including a mode selector 1009 and an actuator 1011. The handpiece 1000 is otherwise configured and used similar to the handpiece 10 of FIGS. 1-3. In this illustrated embodiment, the mode selector 1009 is on a body 1034 of the handpiece 1000, in particular a left side thereof, and is configured as a switch configured to be in one position to select forward impacting and in another, opposite position to select rearward impacting. In this illustrated embodiment, the actuator 1011 is on a handle 1032 of the handpiece 1000, in particular on a forward side of the handle 1032, and is configured as a depressible trigger.

In some embodiments, a surgical impacting tool handpiece can include one or more actuators configured to selectively provide forward impacting or rearward impacting, the surgical impacting tool can be configured to control impact direction either by actuator actuation or by a biasing force applied to the tool by a user, and the handpiece can include a mode selector configured to select a method of impact direction control. Some users may be used to using traditional surgical impacting tools configured to control a direction of impacting based on a biasing force applied to the tool by a user. Thus, a surgical impacting tool being configured to control impact direction in one of two ways as selected by a user may allow the user to use the surgical impacting tool according to the user's known preference. Various surgical impacting tools configured such that a direction of impacting is controlled by a biasing force placed by a user on the tool are further described, for example, in U.S. Pat. Pub. No. 2013/0161050 entitled "Electric Motor Driven Tool For Orthopedic Impacting" published Jun. 27, 2013, U.S. Pat. No. 11,013,503 entitled "Orthopedic Device Delivering A Controlled, Repeatable Impact" issued May 25, 2021, U.S. Pat. No. 11,083,512 entitled "Orthopedic Impacting Device Delivering A Controlled, Repeatable Impact" issued Aug. 10, 2021, U.S. Pat. No. 11,134,962 entitled "Orthopedic Impacting Device Having A Launched Mass Delivering A Controlled, Repeatable & Reversible Impacting Force" issued Oct. 5, 2021, and U.S. Pat. No. 8,393,409 entitled "Electric Motor Driven Tool For Orthopedic Impacting" issued Mar. 12, 2013, which are hereby each incorporated by reference in their entirety.

The mode selector is configured to be operably coupled to a control board (e.g., the control board 38 of FIGS. 4 and 7, or other control board) of the handpiece similar to that discussed above regarding mode selectors configured to select whether actuation of the actuator is configured to provide forward impacting or rearward impacting. Also similar to the mode selectors discussed above regarding impact direction selection, the mode selector configured to select a mode of direction control can have a variety of configurations and can be at various locations on the handpiece, similar to that discussed above regarding first and second actuators.

Referring again to the handpiece 10 of FIGS. 1-3, the handpiece 10 is configured to be releasably attached to a power source (not shown), such as a battery or other power source, to power one or more components of the handpiece 10, such as the motor 28, the control board 38, etc. In this illustrated embodiment, the handle 32 of the handpiece 10 is configured to releasably attach to a power source at a base **32*b* of the handle 32. In other embodiments, the handpiece 10 can be releasably attachable to a power source in another way, such as by being releasably attachable to another portion of the handle 32, releasably attachable to the body 34 of the handpiece 10, or plugged into a power source. In still other embodiments, the power source can be non-releasably attached to the handpiece 10, such as by a battery being non-removably disposed in, e.g., the handle 32**.

The handpiece 10 can include various other features. For example, the handpiece 10 can include an energy selector configured to allow an impact energy level, e.g., high energy or low energy, to be selected by a user. The energy selector can have a variety of configurations and locations, such as a rotary dial, a lever, a button, etc. on the handle 32 of the handpiece 10. Various exemplary embodiments of energy selectors are further described, for example, in U.S. patent application Ser. No. 17/319,700 entitled "Surgical Impacting Tool Interfaces" filed May 13, 2021, which is hereby incorporated by reference in its entirety.

For another example, the handpiece 10 can includes a frequency control configured to allow a frequency of impacts, e.g., slow impacts or fast impacts, to be selected by a user. The energy selector can have a variety of configurations and locations, such as a button, a lever, a rotary dial, etc. on the handle 32 of the handpiece 10. Various exemplary embodiments of frequency controls are further described, for example, in U.S. patent application Ser. No. 17/319,700 entitled "Surgical Impacting Tool Interfaces" filed May 13, 2021 and U.S. Pat. No. 11,013,503 entitled "Orthopedic Device Delivering A Controlled, Repeatable Impact" issued May 25, 2021, which are hereby incorporated by reference in their entirety.

For yet another example, the handpiece 10 can be configured to operate in single impact mode or in multi-impact mode. In multi-impact mode, an actuator (e.g., the first actuator 12, the second actuator 14, or the third actuator 62) is configured to be actuated and held a predetermined threshold amount of time to cause multiple impacts to occur in the selected direction. In single impact mode, an actuator (e.g., the first actuator 12, the second actuator 14, or the third actuator 62) is configured to be actuated then released before passage of the predetermined threshold amount of time so as cause a single impact in the selected direction. Various exemplary embodiments of surgical impacting tool handpieces configured to operate in single impact mode or multi-impact mode are further described, for example, in U.S. Pat. No. 11,134,962 entitled "Orthopedic Impacting Device Having A Launched Mass Delivering A Controlled, Repeatable & Reversible Impacting Force" issued Oct. 5, 2021, which are hereby each incorporated by reference in their entirety.

The handpiece 10 can have additional or alternate features. Various exemplary embodiments of surgical impacting tool handpieces including additional or alternate features are further described, for example, in U.S. patent application Ser. No. 17/319,700 entitled "Surgical Impacting Tool Interfaces" filed May 13, 2021, U.S. Pat. Pub. No. 2013/0161050 entitled "Electric Motor Driven Tool For Orthopedic Impacting" published Jun. 27, 2013, U.S. Pat. No. 10,912,597 entitled "Orthopedic Adapter For An Electric Impacting Tool" issued Feb. 9, 2021, U.S. Pat. No. 11,013,503 entitled "Orthopedic Device Delivering A Controlled, Repeatable Impact" issued May 25, 2021, U.S. Pat. No. 11,083,512 entitled "Orthopedic Impacting Device Delivering A Controlled, Repeatable Impact" issued Aug. 10, 2021, U.S. Pat. No. 11,134,962 entitled "Orthopedic Impacting Device Having A Launched Mass Delivering A Controlled, Repeatable & Reversible Impacting Force" issued Oct. 5, 2021, U.S. Pat. No. 8,393,409 entitled "Electric Motor Driven Tool For Orthopedic Impacting" issued Mar. 12, 2013, U.S. Pat. No. 8,936,105 entitled "Electric Motor Driven Tool For Orthopedic Impacting" issued Jan. 20, 2015, and U.S. Pat. No. 8,695,726 entitled "Electric Motor Driven Tool For Orthopedic Impacting" issued Apr. 15, 2014, which are hereby each incorporated by reference in their entirety.

The surgical impacting tool handpieces described herein that include at least one actuator configured to be actuated by a user to control a direction of impacting regardless of a position of an anvil of the surgical impacting tool handpiece. The actuation of the at least one actuator is configured to control the direction of the impacting, e.g., whether the impacting is in a forward direction or a rearward direction. Thus, unlike some traditional surgical tools such as those discussed above, the intended impacting direction can be achieved regardless of the anvil's position when the at least one actuator is actuated. The actuation of the at least one actuator can therefore be configured to not only control a direction of impacting but movement of the anvil.

Figure 24:
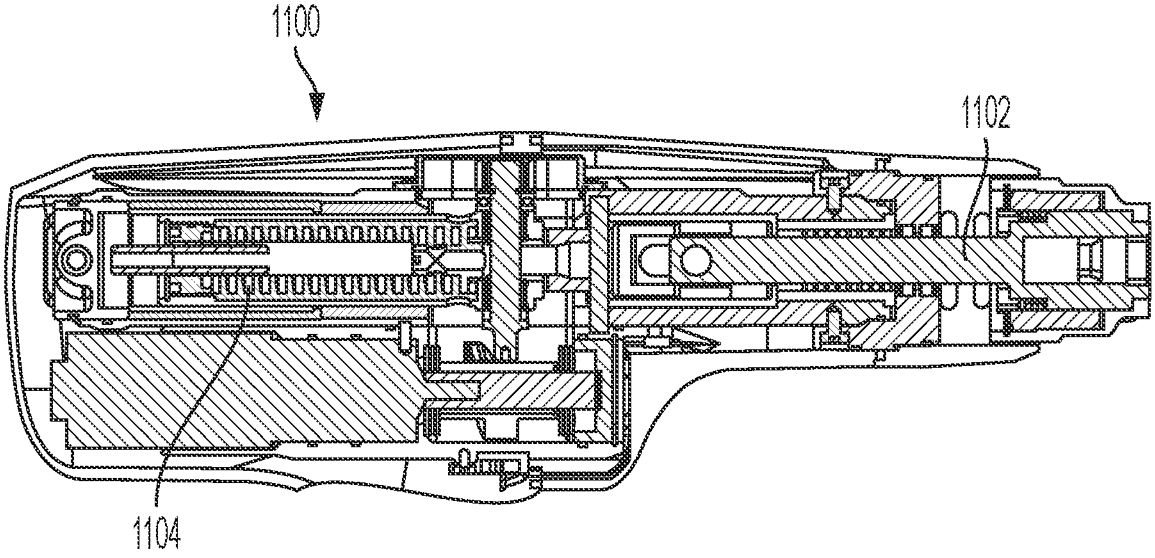
FIG. 24 is a side cross-sectional, partial view of another embodiment of a surgical impacting tool handpiece with an anvil of the handpiece in an extended position.
Figure 25:
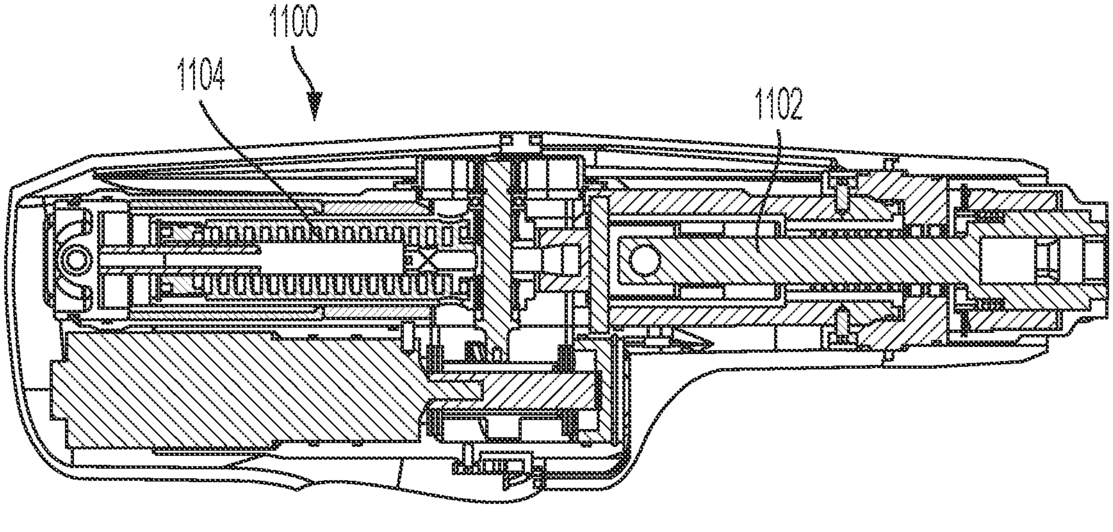
FIG. 25 is a side cross-sectional, partial view of the surgical impacting tool handpiece of FIG. 24 with the anvil in a retracted position.

FIGS. 24 and 25 illustrates an embodiment of a surgical impacting tool handpiece 1100 including an anvil 1102 and at least one actuator. The at least one actuator of the handpiece 1100 is not shown in FIGS. 24 and 25 but can be any of the various actuators described herein. FIG. 24 shows the anvil 1102 in an extended or rearward position in which the anvil 1102 is in a rearmost possible position. Actuation of the at least one actuator to cause rearward impacting is configured to cause the anvil 1102 to be in the extended or rearward position prior to impacting, e.g., to cause the anvil 1102 to move rearward and compress a spring 1104. Once the rearward impact is complete, the anvil is placed in the retracted (forward) position. FIG. 25 shows the anvil 1102 in a retracted or forward position in which the anvil 1102 is in a forward-most possible position. Actuation of the at least one actuator to cause forward impacting is configured to cause the anvil 1102 to be in the retracted or forward position prior to impacting, e.g., to cause the anvil 1102 to move forward due to the spring-loading of the anvil 1102 where decompression of the spring 1104 causes forward movement of the anvil 1102. Once the forward impact is complete, the anvil is placed in the extended (rearward) position.

Figure 26:
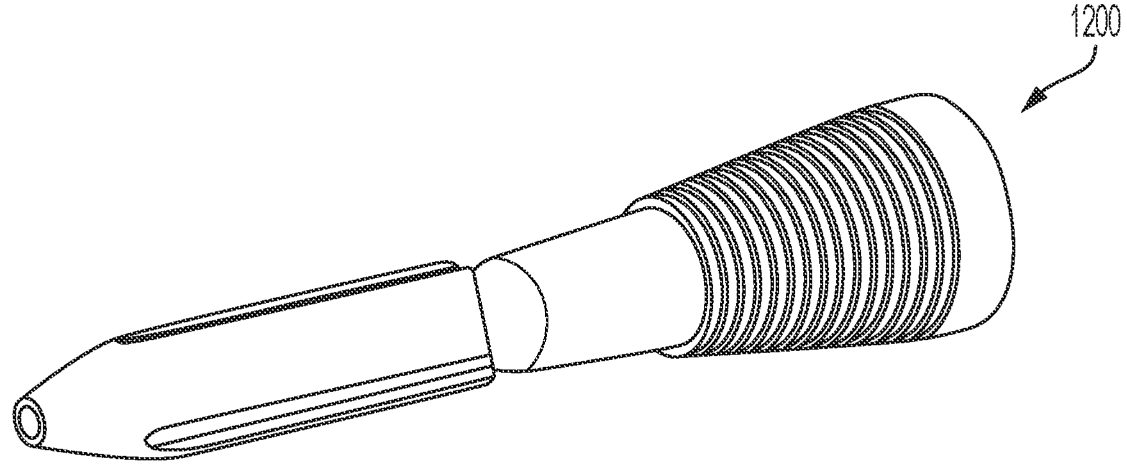
FIG. 26 is a perspective view of one embodiment of a surgical implement.
Figure 27:
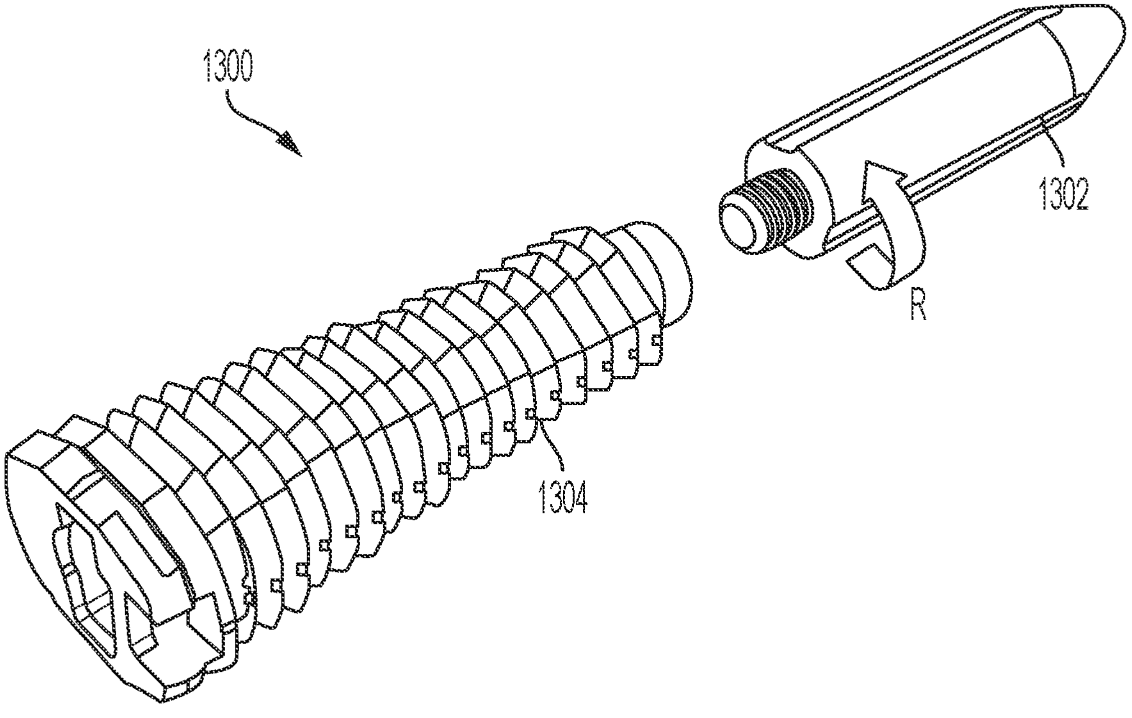
FIG. 27 is a perspective view of another embodiment of a surgical implement.
Figure 28:
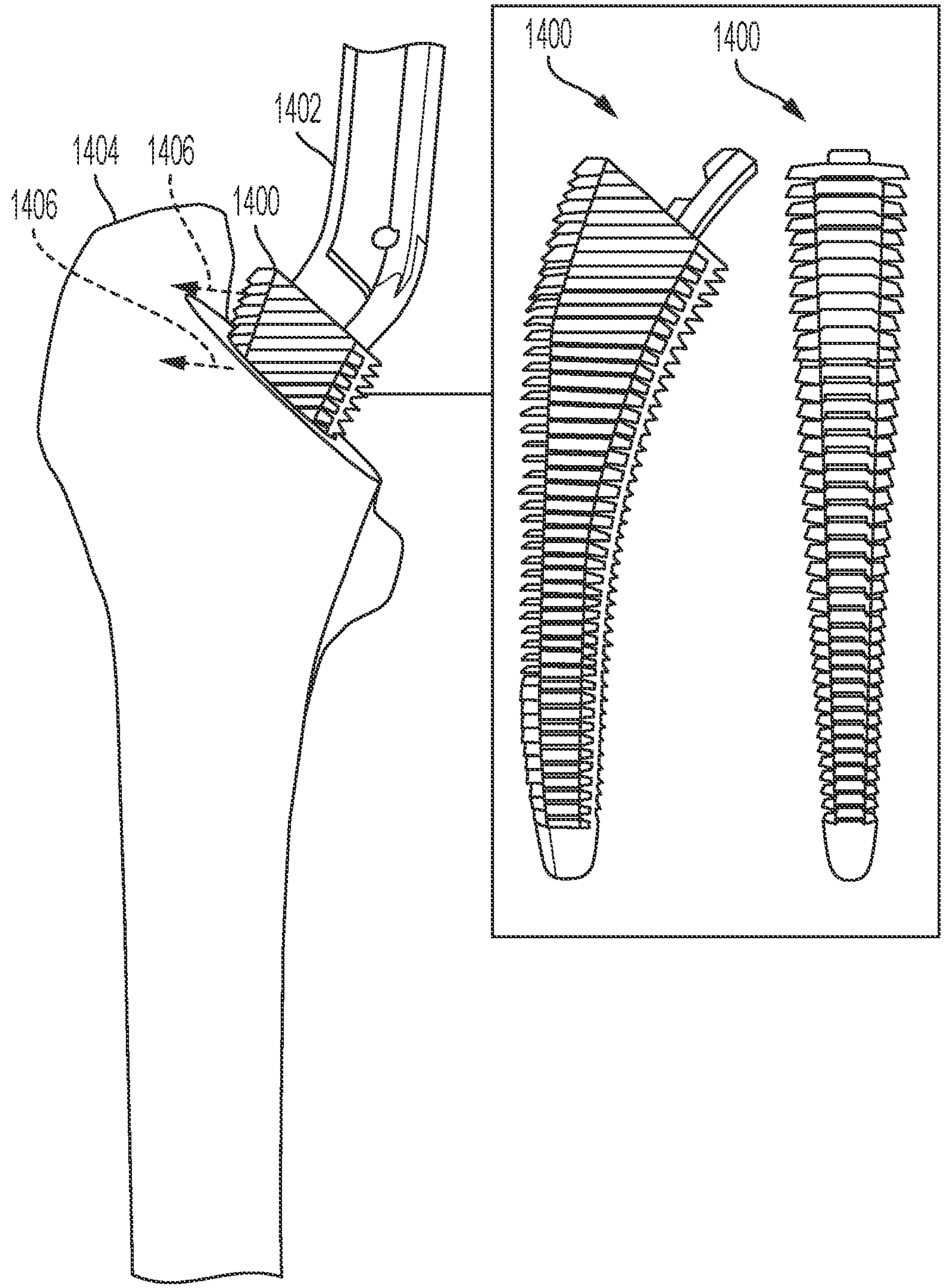
FIG. 28 is a side and end view of yet another embodiment of a surgical implement and a side view of the surgical implement coupled to an adapter and partially inserted into a tibia.

As mentioned above, various surgical implements such as chisels and broaches can be configured to releasably attach to a surgical impacting tool handpiece (e.g., the handpiece 10 of FIGS. 1-3, the handpiece 100 of FIG. 9, the handpiece 200 of FIG. 10, the handpiece 300 of FIGS. 11 and 12, the handpiece 600 of FIG. 19, the handpiece 700 of FIG. 20, the handpiece 800 of FIG. 21, the handpiece 900 of FIG. 22, the handpiece 1000 of FIG. 23, etc.) via an adapter (e.g., the adapter 22 of FIG. 3, an adapter 1302 of FIG. 26, etc.). FIG. 26 illustrates one embodiment of a surgical implement 1200 configured to releasably attach to an adapter. The surgical implement 1200 in this illustrated embodiment is a tibial broach configured for impacting a tibia. FIG. 27 illustrates another embodiment of a surgical implement 1300 configured to releasably attach to an adapter. The surgical implement 1300 in this illustrated embodiment is a femoral broach configured for impacting a femur. The surgical implement 1300 in this illustrated embodiment includes a forward or distal portion 1302 and a rearward or proximal portion 1304 that is configured to releasably attach to the forward portion 1302 by rotating the forward portion 1302 into the rearward portion 1304 as shown by arrow R. FIG. 28 illustrates another embodiment of a surgical implement 1400 configured to releasably attach to an adapter, such as the embodiment of an adapter 1402 illustrated in FIG. 28. As discussed herein, the adapter 1402 can be coupled with a surgical impacting tool handpiece so as to couple the surgical implement 1400 with the surgical impacting tool handpiece. The surgical implement 1400 in this illustrated embodiment is a tibial broach configured for impacting a tibia 1404.

Each of a plurality of surgical implements configured to be attached to an adapter can be different from one another in one or more aspects, such as shape, size, etc., thereby allowing for a particular surgical implement to be selected by a surgeon (or other medical professional) for optimal desired impacting in a particular surgical procedure being performed on a particular patient's bone.

In some embodiments, instead of a surgical implement being releasably attached to an adapter, the surgical implement can be non-releasably attached to the adapter to allow the surgical impacting tool handpiece to be used with a variety of different surgical implements by being attachable to a variety of different adapters.

In some embodiments, instead of an adapter being releasably attached to a surgical impacting tool handpiece, the adapter can be non-releasably attached to the handpiece. The handpiece and the adapter being non-releasably attached together may reduce a number of parts that need to be assembled before the handpiece can be used in impacting bone.

The surgical impacting tools described herein can be used in a variety of surgical procedures, as will be appreciated by those skilled in the art. As mentioned above, in some surgical procedures, a user may want to perform feathering with a surgical impacting tool in which reverse impacting quickly occurs when forwarding impacting is being provided by the tool, or vice versa. For example, in a lateralizing technique, a user may want to perform feathering when trying to broach a canal. In such a lateralizing technique, the surgical implement moves quickly back and forth while a user holding the surgical impacting tool applies pressure laterally to the surgical impacting tool (via the surgical impacting tool handpiece) to press the surgical implement into cancellous bone. Such lateralizing may be accomplished without the user needing to move the handpiece relative to the target bone to accomplish the repeated reverse and forward impacting, unlike some traditional surgical impacting tools where a direction of impacting is accomplished by the user pushing the tool to select forward impacting or pulling the tool to select reverse impacting. Additionally, as discussed above, the feathering may be accomplished by the user actuating one of the tool's first and second actuators while the other of the first and second actuators is already actuated. Accomplishing feathering using such a dual trigger technique may allow the feathering to occur faster than with traditional surgical impacting tools in which the user must push or pull the tool to accomplish the repeated reverse and forward impacting. Faster repeated reverse and forward impacting may help the surgical procedure be performed faster and/or may provide for better impacting of the target.

FIG. 28 illustrates an embodiment of a method of a lateralizing technique. The method is described with respect to the surgical implement 1400 releasably coupled to the adapter 1402 as shown in FIG. 28 but can be similarly performed with other surgical implements and adapters. As mentioned above, the adapter 1402 can be coupled with a surgical impacting tool handpiece, such as surgical impacting tool handpieces described herein. As shown in FIG. 28, the lateralizing technique can be accomplished by the user actuating one of the tool's first and second actuators while the other of the first and second actuators is already actuated, thereby causing tibia 1404 impacting in and out quickly while a lateral side of the canal is broached, as pointed to by arrows 1406.

The devices disclosed herein can be designed to be disposed of after a single use, or they can be designed to be used multiple times. In either case, however, a device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices described herein can be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation or toxic gas that can penetrate the container, such as Ethylene Oxide, gamma radiation, x-rays, or high energy electrons. The radiation kills bacteria on the instrument and in the container. The sterilized instrument can then be stored in the sterile container. The sealed container keeps the instrument sterile until it is opened in a medical facility.

Sterilization can be done by any number of ways known to those skilled in the art including beta or gamma radiation, ethylene oxide, steam, and a liquid bath (e.g., cold soak).

One skilled in the art will appreciate further features and advantages of the devices, systems, and methods based on the above-described embodiments. Accordingly, this disclosure is not to be limited by what has been particularly shown and described, except as indicated by the appended claims. All publications and references cited herein are expressly incorporated herein by reference in their entirety for all purposes.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical device, comprising:

a handpiece configured to be held by a hand, the handpiece being configured to drive impacting of bone, and the handpiece including:

a first actuator configured to be hand-actuated and thereby cause the impacting to be in a forward direction toward the bone; and a second actuator configured to be hand-actuated and thereby cause the impacting to be in a rearward direction away from the bone, the first and second actuators being configured to be actuated independently of one another, and at least one of the first actuator or the second actuator comprising a tactile element configured to distinguish the first and second actuators from one another by feel.

2. The surgical device of claim 1, wherein the handpiece includes a handle configured to be held by the hand; and the first and second actuators are each on one of a forward side of the handle and a rearward side of the handle.

3. The surgical device of claim 1, wherein the handpiece includes a third actuator configured to be hand-actuated and thereby cause the impacting to be in a rearward direction away from the bone.

4. The surgical device of claim 3, wherein the handpiece includes a body and a handle extending from the body, the handle being configured to be held by the hand;

one of the second and third actuators is on the handle; and the other of the second and third actuators is on the body.

5. The surgical device of claim 1, wherein, with one of the first and second actuators actuated, the other of the first and second actuators is configured to be actuated and thereby override a direction of the impacting caused by the actuation of the one of the first and second actuators.

6. The surgical device of claim 1, further comprising a motor operatively coupled to the first and second actuators;

wherein the actuation of the first actuator is configured to cause a first Hall effect sensor to output a first voltage that triggers the motor to move in a first direction; and the actuation of the second actuator is configured to cause a second Hall effect sensor to output a second voltage that triggers the motor to move in a second direction that is opposite to the first direction.

7. The surgical device of claim 6, wherein the first actuator includes a first magnet configured to interact with the first Hall effect sensor in response to the actuation of the first actuator; and the second actuator includes a second magnet configured to interact with the second Hall effect sensor in response to the actuation of the second actuator.

8. The surgical device of claim 1, wherein the first and second actuators each include a depressible trigger.

9. The surgical device of claim 1, wherein the first actuator includes a first element, and the second actuator includes a second element that is pivotally coupled to the first element at a pivot point.

10. A surgical assembly, comprising:

the surgical device of claim 1; and a surgical implement configured to couple to the handpiece, the hand-actuation of the first actuator, with the surgical implement coupled to the handpiece, being configured to cause the surgical implement to be driven in the forward direction, and the hand-actuation of the second actuator, with the surgical implement coupled to the handpiece, being configured to cause the surgical implement to be driven in the rearward direction.

11. A surgical method, comprising:

providing a handpiece configured to be held by a hand, the handpiece being configured to drive impacting of bone, and the handpiece including (i) a first actuator configured to be hand-actuated and thereby cause the impacting to be in a forward direction toward the bone and (ii) a second actuator configured to be hand-actuated and thereby cause the impacting to be in a rearward direction away from the bone, the first and second actuators being configured to be actuated independently of one another;

actuating the first actuator and thereby causing a surgical implement operatively coupled to the first actuator to move forward relative to the bone;

actuating the second actuator, while the first actuator is actuated, and thereby overriding the actuator such that the surgical implement operatively coupled to the second actuator moves rearward relative to the bone; and ceasing actuation of the second actuator, while the first actuator is still actuated, such that the surgical implement moves forward relative to the bone.

12. The method of claim 11, wherein the second actuator is actuated after the first actuator has been actuated.

13. A surgical device, comprising:

a handpiece being configured to drive impacting of bone, and the handpiece including:

a body;

a handle extending from the body, the handle being configured to be held by a hand;

a first actuator configured to be hand-actuated and thereby cause the impacting to be in a forward direction toward the bone;

a second actuator configured to be hand-actuated and thereby cause the impacting to be in a rearward direction away from the bone; and a third actuator configured to be hand-actuated and thereby cause the impacting to be in a rearward direction away from the bone, the first and second actuators being configured to be actuated independently of one another, one of the second and third actuators being on the handle, and the other of the second and the third actuators being on the body.

14. The surgical device of claim 13, wherein the handpiece includes a handle configured to be held by the hand; and the first and second actuators are each on one of a forward side of the handle and a rearward side of the handle.

15. The surgical device of claim 13, wherein, with one of the first and second actuators actuated, the other of the first and second actuators is configured to be actuated and thereby override a direction of the impacting caused by the actuation of the one of the first and second actuators.

16. The surgical device of claim 15, wherein at least one of the first and second actuators includes a tactile element configured to distinguish the first and second actuators from one another by feel.

17. The surgical device of claim 13, further comprising a motor operatively coupled to the first and second actuators;

wherein the actuation of the first actuator is configured to cause a first Hall effect sensor to output a first voltage that triggers the motor to move in a first direction; and the actuation of the second actuator is configured to cause a second Hall effect sensor to output a second voltage that triggers the motor to move in a second direction that is opposite to the first direction.

18. The surgical device of claim 17, wherein the first actuator includes a first magnet configured to interact with the first Hall effect sensor in response to the actuation of the first actuator; and the second actuator includes a second magnet configured to interact with the second Hall effect sensor in response to the actuation of the second actuator.

19. The surgical device of claim 13, wherein the first and second actuators each include a depressible trigger.

20. The surgical device of claim 13, wherein the first actuator includes a first element, and the second actuator includes a second element that is pivotally coupled to the first element at a pivot point.

* * * * *